(12) United States Patent
Grossman

(10) Patent No.: US 11,253,512 B2
(45) Date of Patent: Feb. 22, 2022

(54) OPIOID TAPER REGIMEN

(71) Applicant: Joseph Leon Grossman, Boulder, CO (US)

(72) Inventor: Joseph Leon Grossman, Boulder, CO (US)

( * ) Notice: Subject to any disclaimer, the term of this patent is extended or adjusted under 35 U.S.C. 154(b) by 0 days.

(21) Appl. No.: 16/842,079

(22) Filed: Apr. 7, 2020

(65) Prior Publication Data

US 2020/0316058 A1 Oct. 8, 2020

Related U.S. Application Data

(60) Provisional application No. 62/919,996, filed on Apr. 8, 2019.

(51) Int. Cl.
| | | |
|---|---|---|
| *A61K 31/485* | (2006.01) | |
| *A61K 9/20* | (2006.01) | |
| *A61J 1/03* | (2006.01) | |
| *A61K 9/00* | (2006.01) | |

(52) U.S. Cl.
CPC ............. *A61K 31/485* (2013.01); *A61J 1/035* (2013.01); *A61K 9/006* (2013.01); *A61K 9/20* (2013.01); *A61J 2205/00* (2013.01)

(58) Field of Classification Search
CPC ........ A61K 31/485; A61K 9/006; A61K 9/20; A61K 9/703; A61P 25/00
See application file for complete search history.

(56) References Cited

U.S. PATENT DOCUMENTS

2010/0048535 A1* 2/2010 Slater ...................... A61P 25/30
514/211.13
2011/0288113 A1* 11/2011 Peroutka ................. A61P 25/04
514/282

OTHER PUBLICATIONS

Weinstein, Drug and Alcohol Dependence 189 (2018) 166-171 (Year: 2018).*
Horowitz et al. (Lancet Psychiatry 2019, 6: 538-46, Published online, Mar. 5, 2019) (Year: 2019).*

* cited by examiner

*Primary Examiner* — Umamaheswari Ramachandran

(57) ABSTRACT

A opioid taper regimen, and its method of manufacture, for use in a method of opioid reduction leading to abstinence. Said regimen is administered within the range of 2 to 4 years, or more. The regimen comprises novel approaches to common problems encountered during tapers of low dose opioid addiction. The reduction regimen is generally linear; reduces the dosage level once per week; doses every six hours; reduces doses by steps in the range of about 0.001 to 0.0500 mg; has, near the end, ten weeks of doses of about 0.0025 mg buprenorphine q.i.d.; followed by four or more weeks of placebos. Instructions for manufacture of doses that differ by 0.0025 mg and 0.0050 mg buprenorphine are specified.

7 Claims, 10 Drawing Sheets

|   | 1 | 2 | 3 |   |   |   |   |   |
|---|---|---|---|---|---|---|---|---|
| week # | mg/day | mg/dose | week # | mg/day | mg/dose | week # | mg/day | mg/dose |
| 5 | 2.00 | 0.500 | 39 | 1.32 | 0.330 | 72 | 0.66 | 0.165 |
| 6 | 1.98 | 0.495 | 40 | 1.30 | 0.325 | 73 | 0.64 | 0.160 |
| 7 | 1.96 | 0.490 | 41 | 1.28 | 0.320 | 74 | 0.62 | 0.155 |
| 8 | 1.94 | 0.485 | 42 | 1.26 | 0.315 | 75 | 0.60 | 0.150 |
| 9 | 1.92 | 0.480 | 43 | 1.24 | 0.310 | 76 | 0.58 | 0.145 |
| 10 | 1.90 | 0.475 | 44 | 1.22 | 0.305 | 77 | 0.56 | 0.140 |
| 11 | 1.88 | 0.470 | 45 | 1.20 | 0.300 | 78 | 0.54 | 0.135 |
| 12 | 1.86 | 0.465 | 46 | 1.18 | 0.295 | 79 | 0.52 | 0.130 |
| 13 | 1.84 | 0.460 | 47 | 1.16 | 0.290 | 80 | 0.50 | 0.125 |
| 14 | 1.82 | 0.455 | 48 | 1.14 | 0.285 | 81 | 0.48 | 0.120 |
| 15 | 1.80 | 0.450 | 49 | 1.12 | 0.280 | 82 | 0.46 | 0.115 |
| 16 | 1.78 | 0.445 | 50 | 1.10 | 0.275 | 83 | 0.44 | 0.110 |
| 17 | 1.76 | 0.440 | 51 | 1.08 | 0.270 | 84 | 0.42 | 0.105 |
| 18 | 1.74 | 0.435 | 52 | 1.06 | 0.265 | 85 | 0.40 | 0.100 |
| 19 | 1.72 | 0.430 | 53 | 1.04 | 0.260 | 86 | 0.38 | 0.095 |
| 20 | 1.70 | 0.425 | 54 | 1.02 | 0.255 | 87 | 0.36 | 0.090 |
| 21 | 1.68 | 0.420 | 55 | 1.00 | 0.250 | 88 | 0.34 | 0.085 |
| 22 | 1.66 | 0.415 | 56 | 0.98 | 0.245 | 89 | 0.32 | 0.080 |
| 23 | 1.64 | 0.410 | 57 | 0.96 | 0.240 | 90 | 0.30 | 0.075 |
| 24 | 1.62 | 0.405 | 58 | 0.94 | 0.235 | 91 | 0.28 | 0.070 |
| 25 | 1.60 | 0.400 | 59 | 0.92 | 0.230 | 92 | 0.26 | 0.065 |
| 26 | 1.58 | 0.395 | 60 | 0.90 | 0.225 | 93 | 0.24 | 0.060 |
| 27 | 1.56 | 0.390 | 61 | 0.88 | 0.220 | 94 | 0.22 | 0.055 |
| 28 | 1.54 | 0.385 | 62 | 0.86 | 0.215 | 95 | 0.20 | 0.050 |
| 29 | 1.52 | 0.380 | 63 | 0.84 | 0.210 | 96 | 0.18 | 0.045 |
| 30 | 1.50 | 0.375 | 64 | 0.82 | 0.205 | 97 | 0.16 | 0.040 |
| 31 | 1.48 | 0.370 | 65 | 0.80 | 0.200 | 98 | 0.14 | 0.035 |
| 32 | 1.46 | 0.365 | 66 | 0.78 | 0.195 | 99 | 0.12 | 0.030 |
| 33 | 1.44 | 0.360 | 67 | 0.76 | 0.190 | 100 | 0.10 | 0.025 |
| 34 | 1.42 | 0.355 | 68 | 0.74 | 0.185 | 101 | 0.08 | 0.020 |
| 35 | 1.40 | 0.350 | 69 | 0.72 | 0.180 | 102 | 0.06 | 0.015 |
| 36 | 1.38 | 0.345 | 70 | 0.70 | 0.175 | 103 | 0.04 | 0.010 |
| 37 | 1.36 | 0.340 | 71 | 0.68 | 0.170 | 104 | 0.02 | 0.005 |
| 38 | 1.34 | 0.335 |   |   |   |   |   |   |

Fig. 8

|   | 1 | 2 |   | 3 |   |   |   |   |
|---|---|---|---|---|---|---|---|---|
| week # | mg/day | mg/dose | week # | mg/day | mg/dose | week # | mg/day | mg/dose |
| 5 | 2.00 | 0.500 | 39 | 1.66 | 0.415 | 73 | 1.32 | 0.330 |
| 6 | 1.99 | 0.498 | 40 | 1.65 | 0.413 | 74 | 1.31 | 0.328 |
| 7 | 1.98 | 0.495 | 41 | 1.64 | 0.410 | 75 | 1.30 | 0.325 |
| 8 | 1.97 | 0.493 | 42 | 1.63 | 0.408 | 76 | 1.29 | 0.323 |
| 9 | 1.96 | 0.490 | 43 | 1.62 | 0.405 | 77 | 1.28 | 0.320 |
| 10 | 1.95 | 0.488 | 44 | 1.61 | 0.403 | 78 | 1.27 | 0.318 |
| 11 | 1.94 | 0.485 | 45 | 1.60 | 0.400 | 79 | 1.26 | 0.315 |
| 12 | 1.93 | 0.483 | 46 | 1.59 | 0.398 | 80 | 1.25 | 0.313 |
| 13 | 1.92 | 0.480 | 47 | 1.58 | 0.395 | 81 | 1.24 | 0.310 |
| 14 | 1.91 | 0.478 | 48 | 1.57 | 0.393 | 82 | 1.23 | 0.308 |
| 15 | 1.90 | 0.475 | 49 | 1.56 | 0.390 | 83 | 1.22 | 0.305 |
| 16 | 1.89 | 0.473 | 50 | 1.55 | 0.388 | 84 | 1.21 | 0.303 |
| 17 | 1.88 | 0.470 | 51 | 1.54 | 0.385 | 85 | 1.20 | 0.300 |
| 18 | 1.87 | 0.468 | 52 | 1.53 | 0.383 | 86 | 1.19 | 0.298 |
| 19 | 1.86 | 0.465 | 53 | 1.52 | 0.380 | 87 | 1.18 | 0.295 |
| 20 | 1.85 | 0.463 | 54 | 1.51 | 0.378 | 88 | 1.17 | 0.293 |
| 21 | 1.84 | 0.460 | 55 | 1.50 | 0.375 | 89 | 1.16 | 0.290 |
| 22 | 1.83 | 0.458 | 56 | 1.49 | 0.373 | 90 | 1.15 | 0.288 |
| 23 | 1.82 | 0.455 | 57 | 1.48 | 0.370 | 91 | 1.14 | 0.285 |
| 24 | 1.81 | 0.453 | 58 | 1.47 | 0.368 | 92 | 1.13 | 0.283 |
| 25 | 1.80 | 0.450 | 59 | 1.46 | 0.365 | 93 | 1.12 | 0.280 |
| 26 | 1.79 | 0.448 | 60 | 1.45 | 0.363 | 94 | 1.11 | 0.278 |
| 27 | 1.78 | 0.445 | 61 | 1.44 | 0.360 | 95 | 1.10 | 0.275 |
| 28 | 1.77 | 0.443 | 62 | 1.43 | 0.358 | 96 | 1.09 | 0.273 |
| 29 | 1.76 | 0.440 | 63 | 1.42 | 0.355 | 97 | 1.08 | 0.270 |
| 30 | 1.75 | 0.438 | 64 | 1.41 | 0.353 | 98 | 1.07 | 0.268 |
| 31 | 1.74 | 0.435 | 65 | 1.40 | 0.350 | 99 | 1.06 | 0.265 |
| 32 | 1.73 | 0.433 | 66 | 1.39 | 0.348 | 100 | 1.05 | 0.263 |
| 33 | 1.72 | 0.430 | 67 | 1.38 | 0.345 | 101 | 1.04 | 0.260 |
| 34 | 1.71 | 0.428 | 68 | 1.37 | 0.343 | 102 | 1.03 | 0.258 |
| 35 | 1.70 | 0.425 | 69 | 1.36 | 0.340 | 103 | 1.02 | 0.255 |
| 36 | 1.69 | 0.423 | 70 | 1.35 | 0.338 | 104 | 1.01 | 0.253 |
| 37 | 1.68 | 0.420 | 71 | 1.34 | 0.335 | 105 | 1.00 | 0.250 |
| 38 | 1.67 | 0.418 | 72 | 1.33 | 0.333 | 106 | 0.99 | 0.248 |

Fig. 9A

| week # | mg/day | mg/dose | week # | mg/day | mg/dose | week # | mg/day | mg/dose |
|---|---|---|---|---|---|---|---|---|
| 107 | 0.98 | 0.245 | 140 | 0.65 | 0.163 | 173 | 0.32 | 0.080 |
| 108 | 0.97 | 0.243 | 141 | 0.64 | 0.160 | 174 | 0.31 | 0.078 |
| 109 | 0.96 | 0.240 | 142 | 0.63 | 0.158 | 175 | 0.30 | 0.075 |
| 110 | 0.95 | 0.238 | 143 | 0.62 | 0.155 | 176 | 0.29 | 0.073 |
| 111 | 0.94 | 0.235 | 144 | 0.61 | 0.153 | 177 | 0.28 | 0.070 |
| 112 | 0.93 | 0.233 | 145 | 0.60 | 0.150 | 178 | 0.27 | 0.068 |
| 113 | 0.92 | 0.230 | 146 | 0.59 | 0.148 | 179 | 0.26 | 0.065 |
| 114 | 0.91 | 0.228 | 147 | 0.58 | 0.145 | 180 | 0.25 | 0.063 |
| 115 | 0.90 | 0.225 | 148 | 0.57 | 0.143 | 181 | 0.24 | 0.060 |
| 116 | 0.89 | 0.223 | 149 | 0.56 | 0.140 | 182 | 0.23 | 0.058 |
| 117 | 0.88 | 0.220 | 150 | 0.55 | 0.138 | 183 | 0.22 | 0.055 |
| 118 | 0.87 | 0.218 | 151 | 0.54 | 0.135 | 184 | 0.21 | 0.053 |
| 119 | 0.86 | 0.215 | 152 | 0.53 | 0.133 | 185 | 0.20 | 0.050 |
| 120 | 0.85 | 0.213 | 153 | 0.52 | 0.130 | 186 | 0.19 | 0.048 |
| 121 | 0.84 | 0.210 | 154 | 0.51 | 0.128 | 187 | 0.18 | 0.045 |
| 122 | 0.83 | 0.208 | 155 | 0.50 | 0.125 | 188 | 0.17 | 0.043 |
| 123 | 0.82 | 0.205 | 156 | 0.49 | 0.123 | 189 | 0.16 | 0.040 |
| 124 | 0.81 | 0.203 | 157 | 0.48 | 0.120 | 190 | 0.15 | 0.038 |
| 125 | 0.80 | 0.200 | 158 | 0.47 | 0.118 | 191 | 0.14 | 0.035 |
| 126 | 0.79 | 0.198 | 159 | 0.46 | 0.115 | 192 | 0.13 | 0.033 |
| 127 | 0.78 | 0.195 | 160 | 0.45 | 0.113 | 193 | 0.12 | 0.030 |
| 128 | 0.77 | 0.193 | 161 | 0.44 | 0.110 | 194 | 0.11 | 0.028 |
| 129 | 0.76 | 0.190 | 162 | 0.43 | 0.108 | 195 | 0.10 | 0.025 |
| 130 | 0.75 | 0.188 | 163 | 0.42 | 0.105 | 196 | 0.09 | 0.023 |
| 131 | 0.74 | 0.185 | 164 | 0.41 | 0.103 | 197 | 0.08 | 0.020 |
| 132 | 0.73 | 0.183 | 165 | 0.40 | 0.100 | 198 | 0.07 | 0.018 |
| 133 | 0.72 | 0.180 | 166 | 0.39 | 0.098 | 199 | 0.06 | 0.015 |
| 134 | 0.71 | 0.178 | 167 | 0.38 | 0.095 | 200 | 0.05 | 0.013 |
| 135 | 0.70 | 0.175 | 168 | 0.37 | 0.093 | 201 | 0.04 | 0.010 |
| 136 | 0.69 | 0.173 | 169 | 0.36 | 0.090 | 202 | 0.03 | 0.008 |
| 137 | 0.68 | 0.170 | 170 | 0.35 | 0.088 | 203 | 0.02 | 0.005 |
| 138 | 0.67 | 0.168 | 171 | 0.34 | 0.085 | 204 | 0.01 | 0.003 |
| 139 | 0.66 | 0.165 | 172 | 0.33 | 0.083 | | | |

Fig. 9B

OPIOID TAPER REGIMEN

CROSS-REFERENCE TO RELATED APPLICATIONS

This application claims the benefit of U.S. Provisional Patent Application No. 62/919,996 filed on Apr. 8, 2019, and titled, "Pre-packaged opioid taper kit".

STATEMENT RE: FEDERALLY SPONSORED RESEARCH OR DEVELOPMENT

No federally sponsored research or development.

NAMES OF THE PARTIES TO A JOINT RESEARCH AGREEMENT

Not Applicable.

REFERENCE TO A "SEQUENCE LISTING"

Not Applicable.

PRIOR DISCLOSURES BY THE INVENTOR OR A JOINT INVENTOR

Not Applicable.

BACKGROUND OF THE INVENTION

The present invention is in the field of addiction medicine. The invention is a medication regimen designed to treat an opioid addicted individual who is transitioning from opioid use to opioid abstinence.

The U.S. Department of Health & Human Services (US Dept. HHS in "References," below) reported that in 2016, more than 47,000 people in the United States died from opioid overdoses. Since 1999, more than 500,000 opioid-related deaths have occurred in the United States. In 2017, there were 71,000 Medicare beneficiaries seen as being at serious risk of opioid misuse or overdose (US HHS toolkit)

In recent years, the clinical recommendations and guidelines regarding prescription of opioids have become more conservative, resulting in fewer prescriptions for opioids being written.

One focus of the field of addiction medicine concerns research and treatment into medication protocols intended to facilitate the transition of opioid addicted or habituated human individuals to opioid abstinence.

The term "opioid" describes a plurality of medications. Most patients with opioid dependent conditions who are in treatment programs that meet state or national clinical standards are in maintenance programs. Maintenance programs are designed to provide treatment to an individual for periods sometimes extending to decades or lifetime prescription. A maintenance program most commonly aims to maintain a patient at, or near, a specific dose of medication during an established interval of time. Buprenorphine is widely used in the medication assisted treatment (MAT) of individuals with opioid addiction, opioid dependence, opioid use disorder or other opioid dependent conditions. Buprenorphine is a partial opioid agonist. Its effects of euphoria or respiratory depression are weaker than full opioid agonists such as heroin and methadone (SAMHSA).

Investigations in the fields of addiction medicine and pain medicine include studies that are designed to determine the effectiveness of a method, or various methods, of withdrawal from opioid medication. Investigations can include studies that are designed to test the efficacy or a dose reduction regimen or to compare two or more protocols of dose reduction over time. Withdrawal from medication by a series of gradually reducing doses over time is referred to as "tapering." To reduce an individual's dose over time is to "taper" the individual's dose. The practice of addiction medicine can include prescribing various regimens of dose reduction to individuals who are diagnosed with an opioid addiction, dependence, use disorder or related condition. It would be logical for an individual in conventional MAT to be considered for the protocols described herein, if both clinician and patient desire an abstinence outcome.

The U.S. Department of Health and Human Services (HHS), in 2016, announced that it would significantly expand its training of clinicians regarding prescription of buprenorphine in programs using medication assisted treatment (MAT). The required federal certificate granting a physician permission to treat up to 100 patients for a year or more was increased to permit a physician to treat up to 275 patients with buprenorphine (Bonner).

The use of medication to treat opioid addiction is well-established. Methadone was approved for use in the U.S. to treat pain in 1947. Methadone, for use in what is now termed medication assisted treatment, was approved in 1973. Methadone is a synthetic opioid. Its half-life varies widely among individuals.

The U.S. Dept. of HHS promotes long-term, medication assisted treatment, with the emphasis on maintenance. Among patients, a significant number wish to achieve opioid abstinence. A common view among pain medicine experts is that the path to abstinence is a difficult-to-complete path.

Opioids have many effects in addition to the reduction of pain. In the last few years, the prescribed long-term use of opioids for treating pain, has become less frequent than in years past, in part as a reaction to the incidence of deaths from opioid misuse/overdose. Opioid adverse effects can include constipation, insomnia and reduced libido. Opioids can affect appetite, mood and judgement and reduce irritability. They are being explored for use as an anti-depressant.

Any treatment course that reduces the consumption of opioids will often cause changes in the physiological effects with which opioid administration is associated. Pain can emerge. Mood, appetite, bowel mobility and libido may be affected. Individuals have a significant degree of idiosyncratic response to the many effects of opioids. Opioid metabolism in an individual can be affected by stress levels, metabolic rate, diet, travel, illness, sleep patterns, physical activity, medications and alcohol, among other factors.

Buprenorphine taper protocols or clinical trials generally attempt to taper an individual using an amount of buprenorphine calculated to be at least equivalent to the individual's most recent level of addiction, expressed in relatively precise quantitative terms as regards dosages and time regimen.

The prescribed use of buprenorphine for maintenance and for studies, most commonly uses buprenorphine in combination with naloxone in a ratio of four parts buprenorphine to one-part naloxone (e.g., Suboxone). Naloxone is added to deter diversion and misuse.

Prior Art

The present invention differs from prior art in a number of parameters, including: order of magnitude longer temporal duration; order of magnitude smaller of dose reduction increments; extended dosing at 0.0025 mg, four times a day, for ten weeks, at end of taper, and; four weeks of inert doses following the final buprenorphine doses that address psychological elements of habituation and addiction. No prior art discusses manner of manufacture of their approaches. These differences are seen between the present invention and all of the prior art found.

Taper studies: A number of studies have attempted to determine what constitutes an effective method of tapering opioids to abstinence. Some studies terminated subjects at around an opioid dose equivalent to 2 mg (two milligrams) of buprenorphine per day. "Terminated" here means approximately 2 mg/day was the level of the subjects' final dose. That is generally intended as the starting dose of invention herein. The great majority of these studies tapered subjects over a period of a few weeks to a month or two months. Essentially all, i.e., close to or more than 90%, of the subjects in each study, reverted to opioid use within a few days, weeks or a month or two, following these protocols. Said invention addresses the most likely cause of low efficacy by configuring the dosing regimen so as to reduce the probability of withdrawal symptoms occurring that are sufficiently strong to cause patient regression.

A 2013 study, "A comparison of buprenorphine taper outcomes between prescription opioid and heroin users," (Nielsen) concluded, " . . . patients may taper from buprenorphine as part of a treatment plan". Present invention has a timeframe that is orders of magnitude longer than the studies in Nielson. Dose reduction of present invention, in the 0.0025 to 0.0050 mg/day range, are at least an order of magnitude smaller than those referenced in Nielson.

The timeframe of said invention, e.g., 118 to 218 weeks, or more, is far in excess of the opioid taper research, as found in papers cited. The same, "comparison of buprenorphine taper outcomes" study (Neilson) comparing prescription opioid and heroin users, after a 4-week stabilization phase, used "one of two taper lengths (7 vs. 28 days) to assess the association between taper length and outcome. The perspective in the invention herein presented is 25 to 200 times as lengthy and the present invention is viewed as more likely to adequately address withdrawal issues, which are the predominant cause, by far, of poor efficacy in prior art studies.

A study completed in 2008, "Extended vs short-term buprenorphine-naloxone for treatment of opioid-addicted youth: a randomized trial," (Woody), compared short and long term tapers. Doses in Woody were orders of magnitude larger and duration or taper was two or three weeks. In the present invention dose reduction increments are far smaller and the length of treatment more than 30 times greater in duration.

Reidenberg et al, U.S. Pat. No. 8,637,073 describes a protocol of 12 days or less using buprenorphine patches to treat pregnant opioid users. Present invention differs markedly, as detailed herein, with regards to dosage reduction increments and timeframe.

A 2013 study, "Randomized, Double-blind Evaluation of Buprenorphine Taper Duration in Primary Prescription Opioid Abusers," (Sigmun, Dunn et al) noted the existence of "a recently completed National Institute on Drug Abuse (NIDA) Clinical Trials Network trial that sought to evaluate the efficacy of brief and extended buprenorphine treatment for PO [prescription opioid] abusers" and remarked "that study, which is, to our knowledge, the only other to prospectively evaluate outpatient buprenorphine detoxification for PO abusers, only 6% to 9% of the participants remained abstinent following a 2-week taper." Said invention differs as described in [0020]

A National Institute on Drug Abuse study, ("Adjunctive counseling during brief and extended buprenorphine-naloxone treatment for prescription opioid dependence." by Weiss, 2011) with 653 subjects differs from present invention in the significant parameters described herein.

The NIDA trial referenced above, was the most extensive done up to 2013. The study compared a group that received counseling with a group that did not receive counseling while both groups were tapering-off of buprenorphine. The study concluded that, " . . . if tapered off buprenorphine-naloxone, even after 12 weeks of treatment, the likelihood of unsuccessful outcome is extremely high, even among patients receiving counseling in addition to medical management." "Extremely high," here equated to 92 (ninety-two) percent did not stop use of opioids.

Patents, all of which differ, as described above in [0020]: Peroutka, patent Ser. No. 12/952,823, for a method to reduce or eliminate a tolerance-inducing agent, states that 28 (twenty eight) days are required to withdraw from a 60 (sixty) mg morphine starting dose. Present invention tapers from equivalent of 60 mg morphine, equivalent to 2 (two) mg of buprenorphine, has a duration of 826 (eight hundred and twenty-six) days, i.e., 118 weeks. Compare 28 days (Peroutka) with 826 days for present invention. Present invention allows approximately 30 times as long, (826/30=29.5) for taper to succeed. Peroutka and present invention are two significantly different approaches. No method for manufacture is provided in Peroutka. Present invention also combines longer times and smaller dose reductions with more frequent dosing and a period of administration of inert doses as a period to permit psychological withdrawal, all elements that are not found previously. Details of 118-week regimen discussed above.

Present invention addresses dose reduction with a precise regimen of reducing doses in which reduction increment is smaller than in prior art. Present invention decreases doses weekly in the range of 0.01 to 0.02 per week of mg buprenorphine, i.e., reductions in divided doses four times per day of 0.0025 and 0.0050. Pergolizzi, US2012/037619, presents a reduction in 5 mg increments of hydrocodone, which is equivalent to about 0.17 mg buprenorphine using 30 to 1 equivalency of buprenorphine/morphine. Pergolizzi dosage increment is eight to 16 times the interval of dose reduction in the present invention's 118-week and 218-week regimens, respectively, herein. Pergolizzi illustrations of medication cards shows that this reduction is intended to be accomplished in seven days. Combining the rate of Pergolizzi dose reduction of about 8 to 17 times greater in magnitude with the length of time, which is 118 to 218 times as great in present invention, Pergolizzi's attempted rate of reduction is 944 to 3706 times as rapid.

Pergolizzi includes reducing hydrocodone from 7.5 mg of hydrocodone on day three to 5.0 mg of hydrocodone on day four. This is equivalent to reducing from 0.25 to 0.17 mg buprenorphine in one day. This reduction of equivalent of 0.08 mg buprenorphine in one day is equal to the reduction in present invention herein of four to eight weeks. The present invention is built upon a different set of principles than Pergolizzi. These two inventions are not similar other than both reduce medication over a period of time. The present invention describes a method of manufacture, whereas, Pergolizzi does not.

The present invention herein discusses reductions in the range of 0.01 to 0.02 mg buprenorphine per week whereas Slater et al, discusses buprenorphine dose reduction in the range of "1.0-0.01 mg per day." Slater administers buprenorphine at intervals of 24-48 hours. Present invention adheres to every six hours with basis grounded in accepted understanding of half-life of buprenorphine and accepted point at which withdrawal symptoms are generally accepted to arise in a significant percentage of the population, i.e., around the point of 10 (ten) percent reduction of physiologically available opioid. Present invention details method of manufacture, whereas in Slater there is no presentation of method of manufacture.

The present invention is mindful of the rate at which the human body is capable of moving from an opioid addicted state to being opioid free, without inducing counter-productive levels of withdrawal. In summary re prior art: Specifics and orders of magnitude of dose reductions and durations of time at each step of dosing show present invention as significantly different from prior art. Manner of manufacture is specified in present invention.

REFERENCES AND PATENTS

Arch Gen Psychiatry. 2011 December; 68 (12):1238-46. doi: 10.1001/archgenpsychiatry.2011.121. Epub 2011 Nov. 7.

Bain K T, Holmes H M, Beers M H, Maio V, Handler S M, Pauker S G. Discontinuing Medications: A Novel Approach for Revising the Prescribing Stage of the Medication-Use Process *J Am Geriatr Soc.* 2008; 56(10): 1946-52.

Bi M, Sun C C, Alvarez F, Alvarez-Nunez F. The manufacture of low-dose oral solid dosage form to support early clinical studies using an automated micro-filing system. AAPS PharmSciTech. 2011; 12(1):88-95. doi:10.1208/s12249-010-9549-y Centers for Disease Control and Prevention. Data Brief 294. Drug Overdose Deaths in the United States, 1999-2016. Accessed Feb. 26, 2020. https://www.cdc.gov/nchs/data/databriefs/db294_table.pdf#page=1

Centers for Medicare and Medicaid Services. Prescription drug coverage contracts. Opioid Oral Morphine Milligram Equivalent (MME) Conversion Factors. https://www.cms.gov/Medicare/Prescription-Drug-Coverage/PrescriptionDrugCovContra/Downloads/Opioid-Morphine-EQ-Conversion-Factors-Aug-2017.pdf Dunn, K. E., Sigmon, S. C., Strain, E. C., Heil, S. H., & Higgins, S. T. (2011). The association between outpatient buprenorphine detoxification duration and clinical treatment outcomes: a review. Drug and Alcohol Dependence, 119(1-2), 1-9.

Horowitz, M A., Taylor, D. The Lancet, Psychiatry, V.6 p. P538-546, 1 Jun. 2019 Loren Bonner. HHS expands buprenorphine access. Pharmacy Today. September 2016 https://www.pharmacytoday.org/article/S1042-0991(16)30819-2/pdf Ling, W., Hillhouse, M., Domier, C., Doraimani, G., Hunter, J., Thomas, C., . . . & Selzer, J. (2009). Buprenorphine tapering schedule and illicit opioid use. Addiction, 104(2), 256-265.

Nielsen S, Hillhouse M, Thomas C, Hasson A, Ling W. A comparison of buprenorphine taper outcomes between prescription opioid and heroin users. *J Addict Med.* 2013; 7(1):33-8.

*Pergolizzi, J. et al. Package for improved treatment of conditions; Inventors: Joseph Pergolizzi, Maninder Chopra; Edmundo Muniz; Neil Flanzraich. US20120289534A1. Assigned to KIRAX CORP

*Peroutka, S J. Method to reduce or elminate [sic] the use by a patient of a tolerance-inducing pharamacological agent; Inventor: Stephen J. Peroutka, application Ser. No. 12/952,823; US20110288113A1; Filed: Nov. 23, 2010.

SAMHSA. Substance Abuse and Mental Health Services Administration.Buprenorphine is used in medication-assisted treatment (MAT) to treat Opioid Use Disorder (OUD). https://www.samhsa.gov/medication-assisted-treatment/treatment/buprenorphine. Accessed Mar. 10, 2020.

Sigmon, S. C., Dunn, K. E., Saulsgiver, K., Patrick, M. E., Badger, G. J., Heil, S. H., & Higgins, S. T. (2013). A randomized, double-blind evaluation of buprenorphine taper duration in primary prescription opioid abusers. JAMA psychiatry, 70(12), 1347-1354.

*Slater, K C, et al. Drug detoxification protocol using microdosing; European Patent Applicant. Application number: 08002803.8; Slater, Kenneth C.; Richardson, Brenda E; Connors, Manchester M A; Connors, Scott M. Methuen M A; Priority: 15.02.2007 US 675560;

Umbricht, A., Montoya, I. D., Hoover, D. R., Demuth, K. L., Chiang, C. T., & Preston, K. L. (1999). Naltrexone shortened opioid detoxification with buprenorphine. Drug and alcohol dependence, 56(3), 181-190.

U.S. Department of Health & Human Services Office of Inspector General Toolkit: Using Data Analysis To Calculate Opioid Levels and Identify Patients At Risk of Misuse or Overdose. June 2018 OEI-02-17-00560. Page 1. https://oig.hhs.gov/oei/reports/oei-02-17-00560.pdf Weiss R D, et al. Adjunctive counseling during brief and extended buprenorphine-naloxone treatment for prescription opioid dependence: a 2-phase randomized controlled trial. Arch Gen Psychiatry. 2011 December; 68(12):1238-46. doi: 10.1001/archgenpsychiatry.2011.121. Epub 2011 Nov. 7

Woody G E, Poole S A, Subramaniam G, et al. Extended vs short-term buprenorphine-naloxone for treatment of opioid-addicted youth: a randomized trial Jama, 2008—jamanetwork.com World Health Organization, Information sheet on opioid overdose/https://www.who.int/substance_abuse/information-sheet/en/accessed Feb. 24, 2020.

BRIEF SUMMARY OF THE INVENTION

The scope of the present invention is defined solely by the appended claims and detailed description of a preferred embodiment, and is not affected to any degree by the statements within this summary.

This invention is a medication regimen designed to be prescribed for the purpose of allowing an individual to reduce, in an orderly and controlled manner, through the use of buprenorphine, or equivalent medication, their opioid consumption to the point of zero opioid usage. All references to milligrams (mg), unless otherwise noted, are milligrams of buprenorphine.

The embodiment of this invention comprises a course of opioid medication, in a packaged kit, as described below. The method of manufacturing the doses is stated because producing doses that consistently and predictably differ by 0.0025 or 0.0050 mg of buprenorphine poses novel challenges.

The range of regimens are 100 to 900 weeks with specific regiments described in the range of 118 weeks to 218 weeks. Various milligram (mg) starting points may be selected outside the range shown herein through use of the dosage reduction steps and manufacture methods described herein. The invention comprises:

1) blister packs of 28 doses, one dose administered every six hours, with each blister pack containing doses for one week, i.e., 168 hours, being 28 doses, one every six hours;

2) is designed to utilize buprenorphine as the active agent or an opioid with a longer half-life than buprenorphine;

3) starts when a patient is stabilized for four weeks at a dose of 2 (two) mg buprenorphine per day, in four divided doses, with patients also starting at higher or lower doses than 2 mg/day total of buprenorphine;

4) with two options described in detail herein, each with a constant linear reduction, one being a reduction each week equal to 0.02 (two one-hundredths) mg of buprenorphine, requiring 100 (one hundred) weeks when starting at 2.00 (two) mg, and a second option of reduction each week equal to 0.01 (one one-hundredth) mg per week, with this regimen requiring 200 (two hundred) weeks of a reduction phase when starting at a total daily dose of 2.00 (two) mg;

5) the manufacturing details herein for starting at 2 mg/day total but may be applied to any starting point.

After 100 weeks of tapering the daily dose of the 0.02 (two one-hundredths) mg reduction per week, after the regimen reaches 0.02 mg buprenorphine per day, in four divided doses per day, for a week, the total daily dose is reduced to 0.01 mg/day buprenorphine for 10 (ten) weeks. See illustrations.

After 200 weeks of tapering the daily dose of the 0.01 (one one-hundredth) mg reduction per week, after the regimen reaches 0.01 mg buprenorphine per day, in four divided doses per day, for a week, the total daily dose is continued at 0.01 mg/day buprenorphine for 10 (ten) weeks. See illustrations.

Following ten weeks of administration of 0.01 mg of buprenorphine per day, total, in four divided doses, i.e., q.i.d., the dose reduces to zero opioid in a doubly unblinded inactive dose. After the first week of the four weeks of dosing with a pharmacologically inert dose every six hours, there is one week of three times a day, one week of b.i.d., and one week of once a day inert doses.

The regimen and the manufacture of regimen may modified to start at higher doses, such as 3 (three) mg or 4 (four) mg buprenorphine per day, in four divided doses, retaining the reductions of 0.01 mg or 0.02 mg per week. Starting at 3 mg daily total dose of buprenorphine and reducing by 0.01 or 0.02 mg/week, these regimens will require about six and three years respectively. Starting at 4 mg daily total dose of buprenorphine and reducing by 0.01 or 0.02 mg/week, these regimens require about eight and four years respectively. All regimens have a four-week stabilization entry point and end with 10 weeks of 0.01 mg daily total, in four divided doses, plus four weeks of open-label inert doses, as described above, decreasing from 4× day, to 3× day, to 2× day to 1× day.

Precision product manufacture is required to achieve the small decrements. A method to ensure uniform production throughout the entire kit sequence of, e.g., 118, 218, 418 or more weeks, is described herein and requires that manufacture from the same lot of buprenorphine. materials, as described below. The embodiment of a full kit consists of, for example, 118 or 218 blister packs, of 28 doses each, for the 2 mg starting points with 0.01 and 0.02 mg/week reduction. The 28-dose blister packs have a tear-off tab that permits four doses, i.e., one day's supply, to be detached, at one time, for use, one dose every six hours.

This invention is designed to be most effective when utilizing buprenorphine and opioids with a shorter half-life are not suitable.

This invention addresses problems caused by the ultra-sensitivity to dose reduction at relatively low doses, e.g. at approximately 2.0 mg/day total and less, among a significant number of patients. This invention is novel in that it addresses withdrawal that emerges among some patients as early as six hours. A half-life calculation demonstrates that after six hours, buprenorphine has dropped about ten percent from the previous dose, in patients in which buprenorphine has the generally accepted value for buprenorphine half-life of 37 hours. A ten percent drop is considered sufficient to cause withdrawal symptoms.

Methods of manufacture: 1) Portion-removal of compound followed by reconstitution to the original mass using inert matter (portion-removal/reconstitution): Comprises a method by which a series of gradually reducing doses can be manufactured when the difference between sequential doses must be maintained at intervals of 0.0025 mg difference across a range of from 8 mg to 0.0025 mg with specific instructions provided for the range of 2 mg down to 0.0025 mg. 2) Film cutting: a method by which film can be cut into pieces and assembled to produce exact doses. 3) The traditional approach of mixing separate batches while varying active ingredients in order to achieve a range of doses in a tablet of fixed mass.

Manufacture, General Points:

Specialized production techniques are described to address the small amounts of dose reduction from one week to the next. This is novel, in part because dosage regimens with the dose-to-dose increments of the magnitude described herein have not been manufactured. With the 0.01 mg/week reduction regimen, the reductions require each of the four divided doses per day to be reduced by 0.0025 (twenty-five ten-thousandths) mg, when comparing one divided dose with the previous week's divided dose. Traditional methods are described of mixing known quantities in appropriate ratios.

Opioids claimed as equivalents are listed herein. The invention is designed to be utilized with buprenorphine without naloxone but may be utilized with the standard 4 units buprenorphine to 1 unit naloxone mixture. Morphine footnote: Conversion tables from the U.S. Centers for Disease Control (CDC), and from sources cited here, show buprenorphine tablet to morphine milligram equivalents as a ratio of 1 mg buprenorphine equal to 30 milligrams of morphine.

BRIEF DESCRIPTION OF THE DRAWINGS

FIG. 8 shows the specific doses in the 100 weeks, 5 through 104, of the 118-week regimen during which there is a 0.02 mg buprenorphine reduction per week in the daily dose.

FIGS. 9A and 9B shows the specific doses in the 200 weeks, weeks 5 through 214, of the 218-week regimen during which there is a 0.01 mg buprenorphine reduction per week of the daily dose.

DETAILED DESCRIPTION OF THE DRAWINGS

Figure 1:
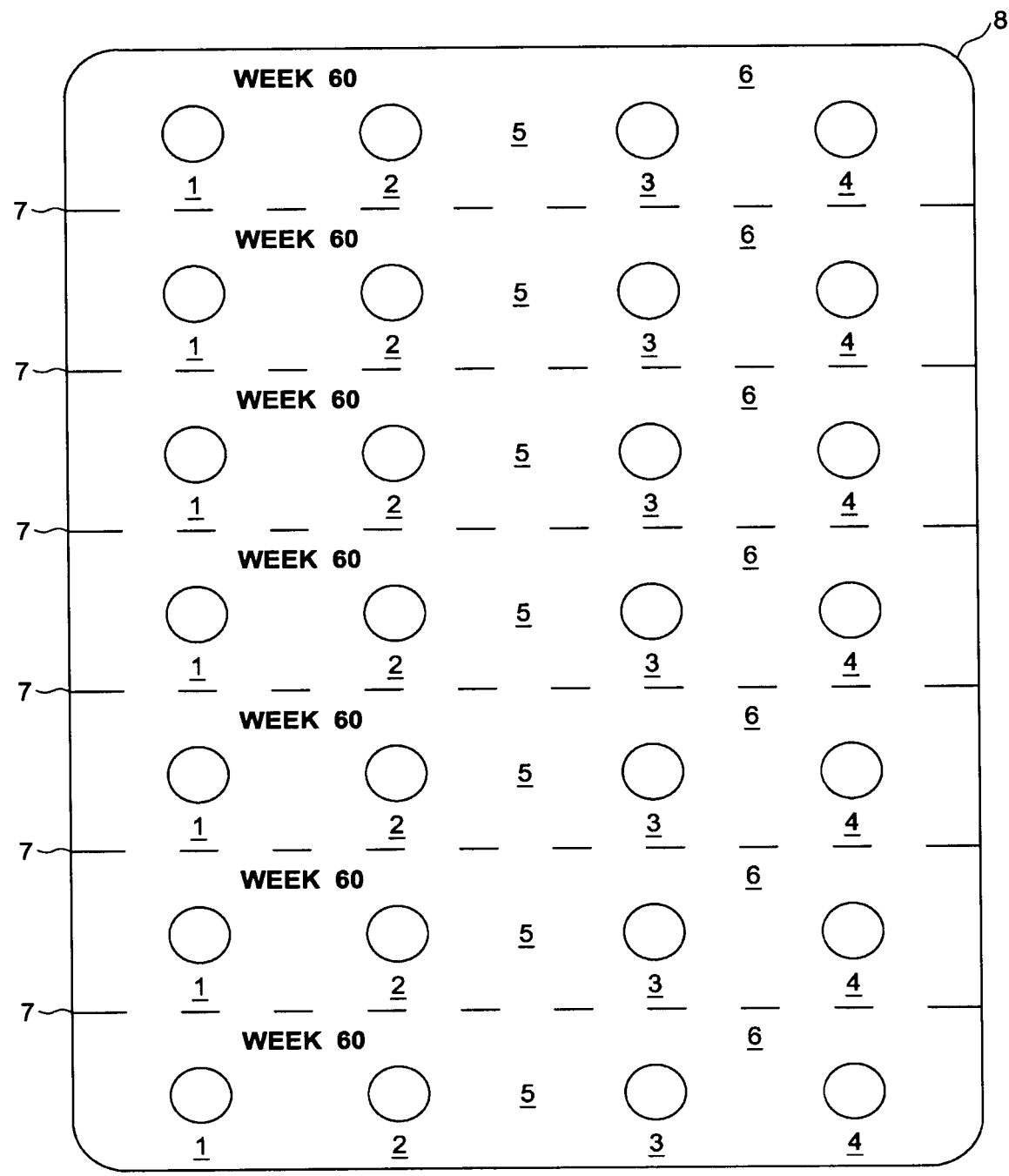
FIG. 1 shows one representative blister pack which is a card with 28 doses of medication.

FIG. 1 shows a diagram of a blister pack 8 containing 28 doses of opioid, each of the 28 doses containing the same amount of medication, which 28 doses being one week of medication, with four doses for each day, the numbers 1, 2, 3, and 4 appearing under the circles representing the doses and indicated where the amount of each dose is printed under the blister for that dose, e.g., 0.225 mg buprenorphine. 5 indicates where the Day of the week is shown as, Day 1, Day 2, Day 3, Day 4, Day 5, Day 6 and Day 7.

The medication for Days 1 through 7 of each week is in detachable strips holding four doses each, intended for dosing every six hours. 7 shows serrations between the strips, allowing the seven daily strips to be separated. Each day, Days 1 through 7, a strip may be detached along a perforated line such that four doses (24 hours) may be carried about without carrying doses for seven days.

The total daily dose is indicated, 6, on every strip, e.g. "0.9 mg buprenorphine per day in four doses." The blister pack card is the size of a standard credit/debit card, being about 2.125 inches by 3.375 inches, or larger. Each card has the week of the regimen printed on each of the seven strips, in the largest and boldest font on the card, e.g. Week 60, to insure that the four cards normally dispensed at one time are utilized in the correct sequence, e.g., Week 60, Week 61, Week 62, Week 63. See FIG. 4 for how four cards dispensed at one time appear.

Figure 2:
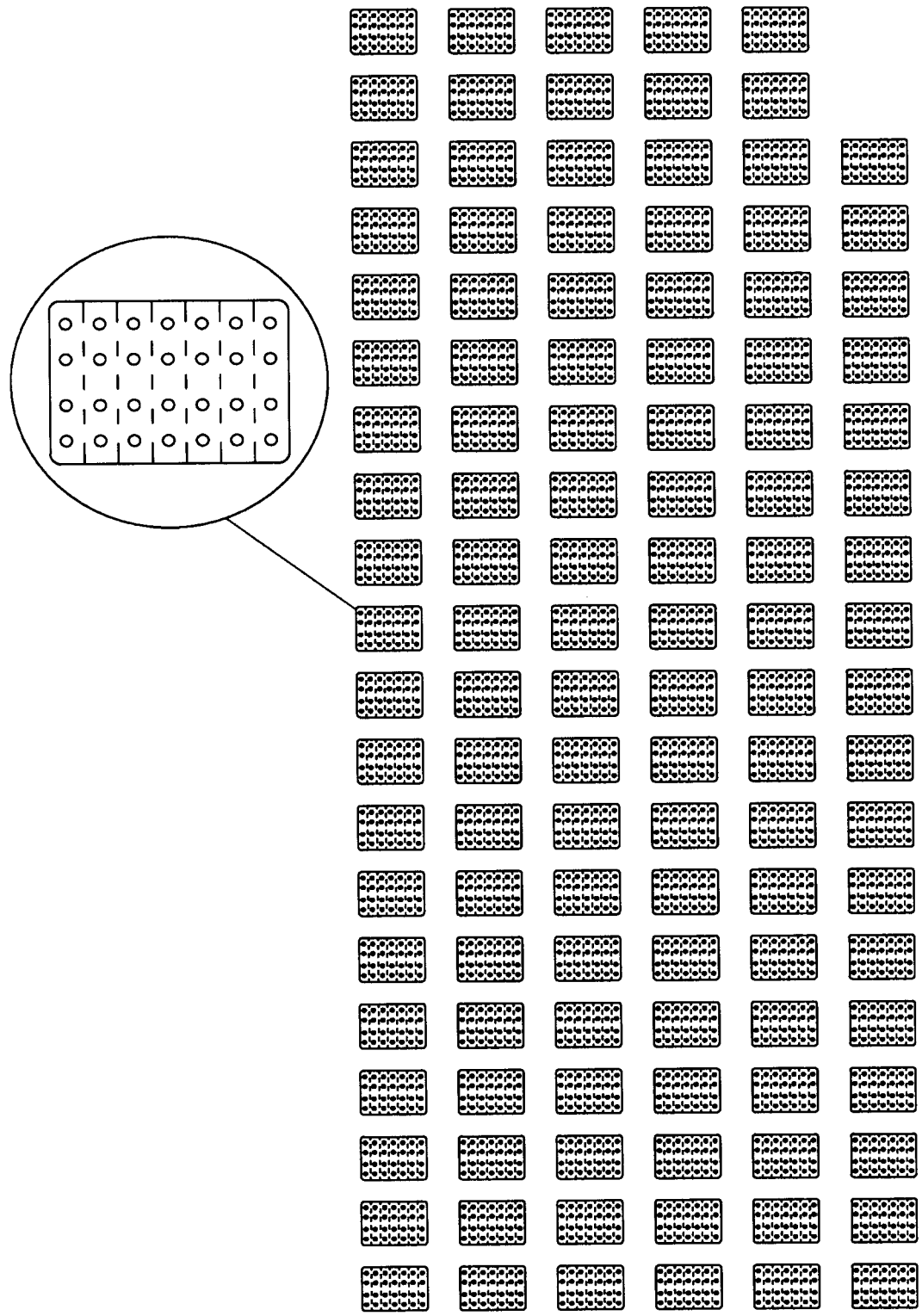
FIG. 2 is a diagrammatic representation of the blister pack cards of a 118-week regimen of decreasing doses of buprenorphine or equivalent, as described herein.

FIG. 2 shows an overviews of 118 medication blister packs, representing 118 weeks of a packaged, opioid taper kit and shows in diagrammatic format, how an entire 118-week kit appears when displayed at one time. There is an exploded view of one of the 118-cards, all of which are identical in construction and contain a regimen of opioid doses that, when it changes, decreases in a sequential manner on a weekly basis. Dosage amounts shown in FIG. 8.

Figure 3:
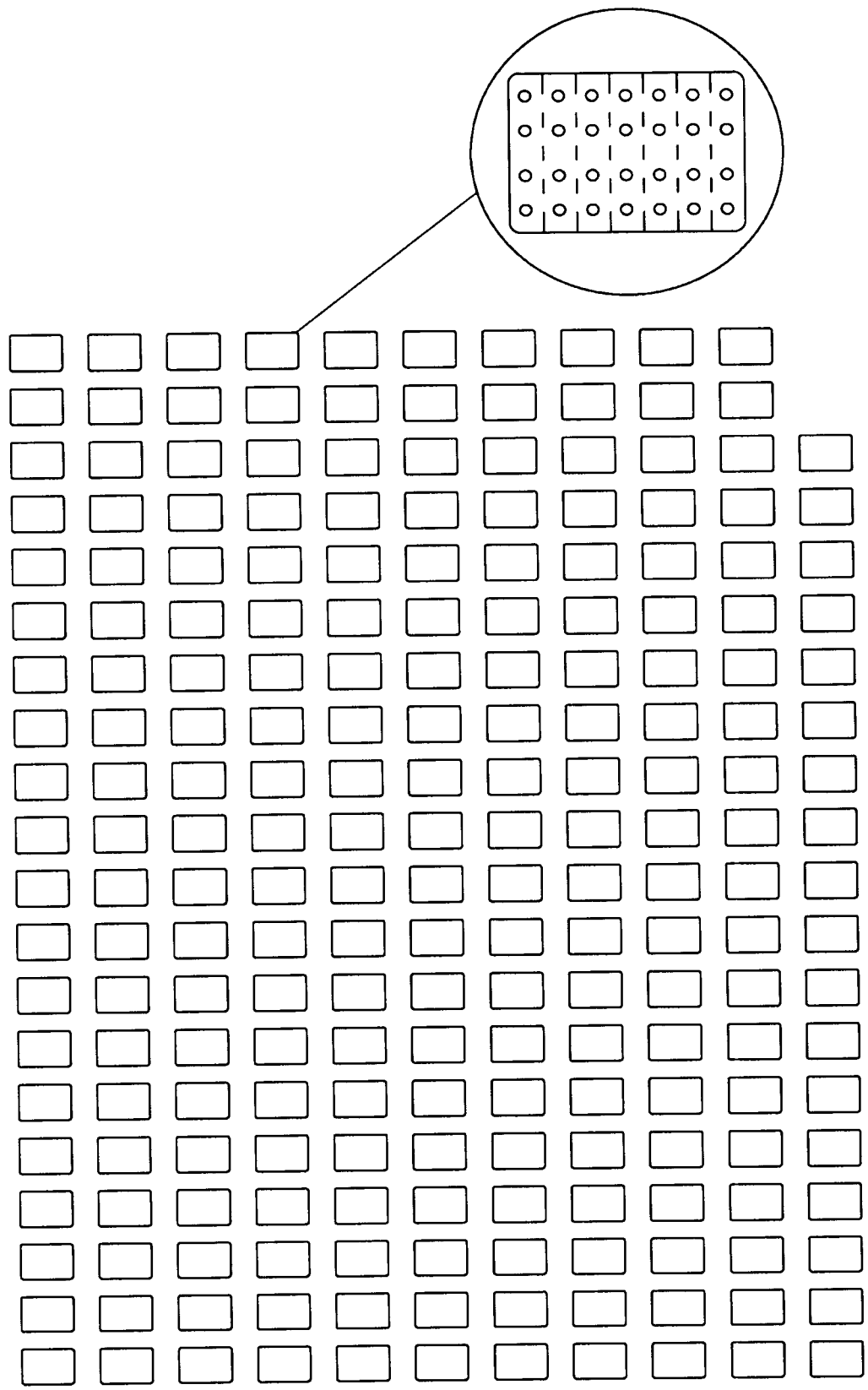
FIG. 3 is a diagrammatic representation of the blister pack cards of a 218-week regimen of decreasing doses of buprenorphine.

FIG. 3 is an overviews of 218 medication blister packs, representing 218 weeks of a packaged, opioid taper kit and shows in diagrammatic format, how an entire 218-week kit appears when displayed at one time. There is an exploded view of one of the 218-blister pack cards, all of which are identical in construction and contain a regimen of opioid doses that, when the dose changes, decreases in a sequential manner on a weekly basis. Dosage amounts shown in FIGS. 9A and 9B.

Figure 4:
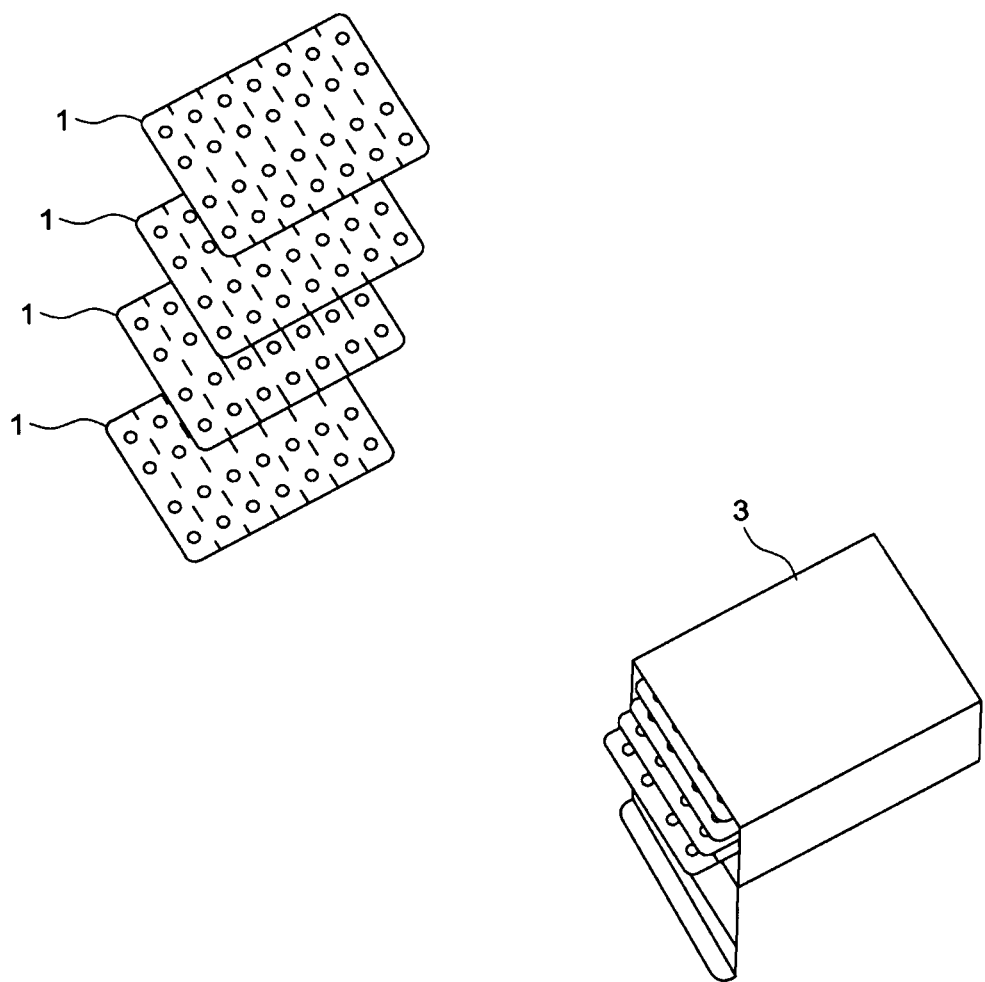
FIG. 4 shows a view of four blister packs of opioid taper and also shows the four blister packs in a box. This represents doses for four weeks.

FIG. 4 is a view of four blister packs and also shows the four blister packs in a box. This is how the medication appears when dispensed and a monthly basis, the norm for many buprenorphine preparations.

Figure 5:
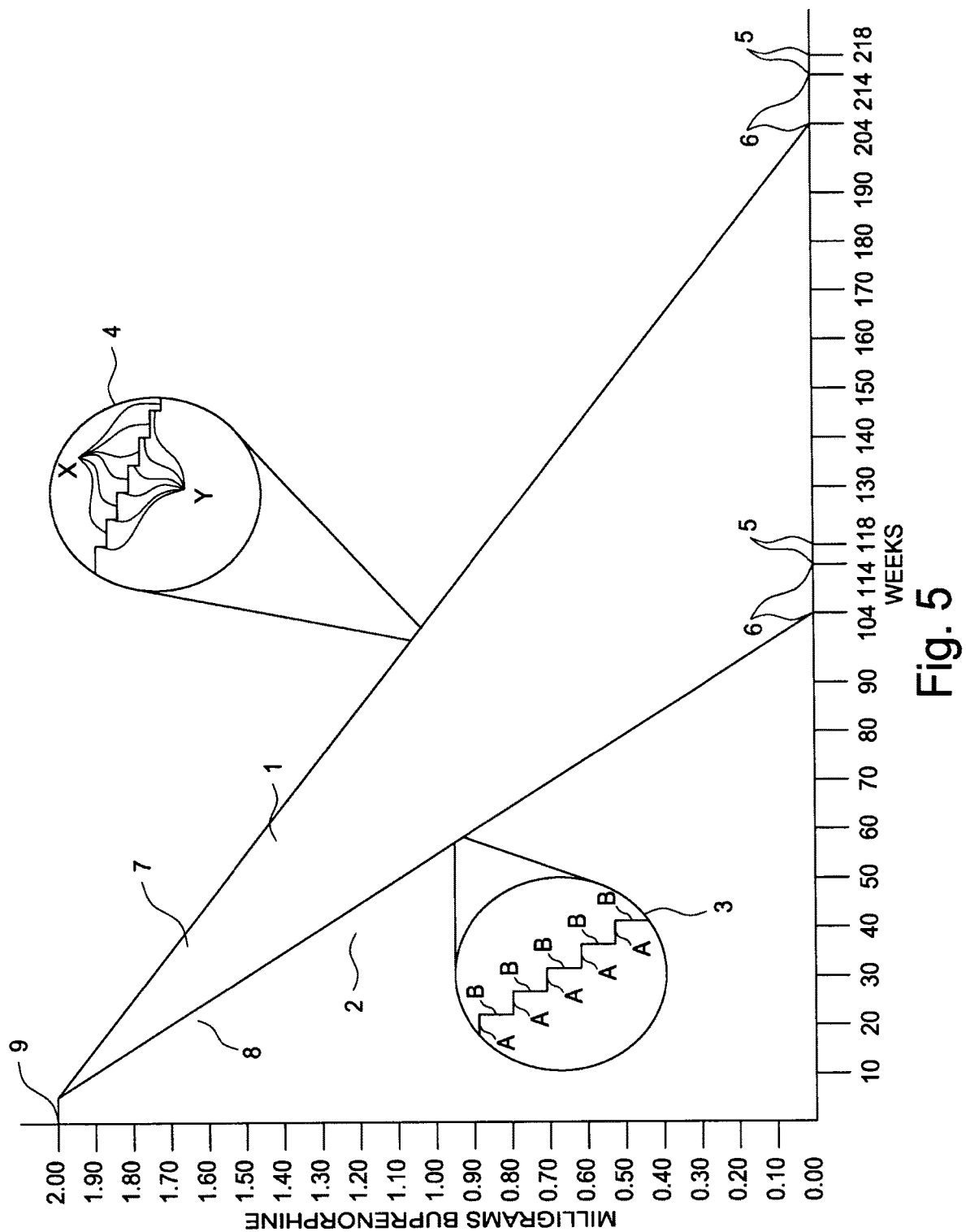
FIG. 5 is a graph plotting doses (y-axis) over time (x-axis) for 118 and 218-week regimens.

FIG. 5 is a graph of dosage on the y-axis, in milligrams of buprenorphine, against time in weeks, on the x-axis. A four-week period initial period of weeks 1 through 4, indicated by 9, is common to both regimens shown by 1 and 2. During the four weeks, in this specific regimen, the initial dosage is 2 mg per day of buprenorphine, in four divided doses.

1 is the 218-week regiment and 2 is the 118-week regimen. 7 is 0.01 mg buprenorphine per week reduction which runs from start of Week 5 through end of Week 204. 8 is 0.02 mg buprenorphine per week reduction which runs from start of Week 5 through end of Week 104.

6 is a period during which the daily dose total is 0.01 mg of buprenorphine. This applies in the 218-week regimen for weeks 205 through 214 and in the 118-week regimen for weeks 105 through 114.

5 is a 4-week period during which open-label inert doses are prescribed. This applies in the 218-week regimen for weeks 215 through 218 and in the 118-week regimen for weeks 115 through 118.

4 is an exploded view showing what is represented by straight line 1 for weeks 5 through 214 consists of weekly reductions of doses, with each week being indicated by an X and each weekly dosage decrease of 0.01 (one one-hundredth) mg indicated by a Y.

3 is an exploded view showing what is represented by straight line 2 for weeks 5 through 114 consists of weekly reductions of doses, with each week being indicated by A and each weekly dosage decrease of 0.02 (two one-hundredths) mg indicated by B. See FIG. 8 for doses weeks 5 through 104. See FIGS. 9A and 9B for doses weeks 5 through 204.

Figure 6:
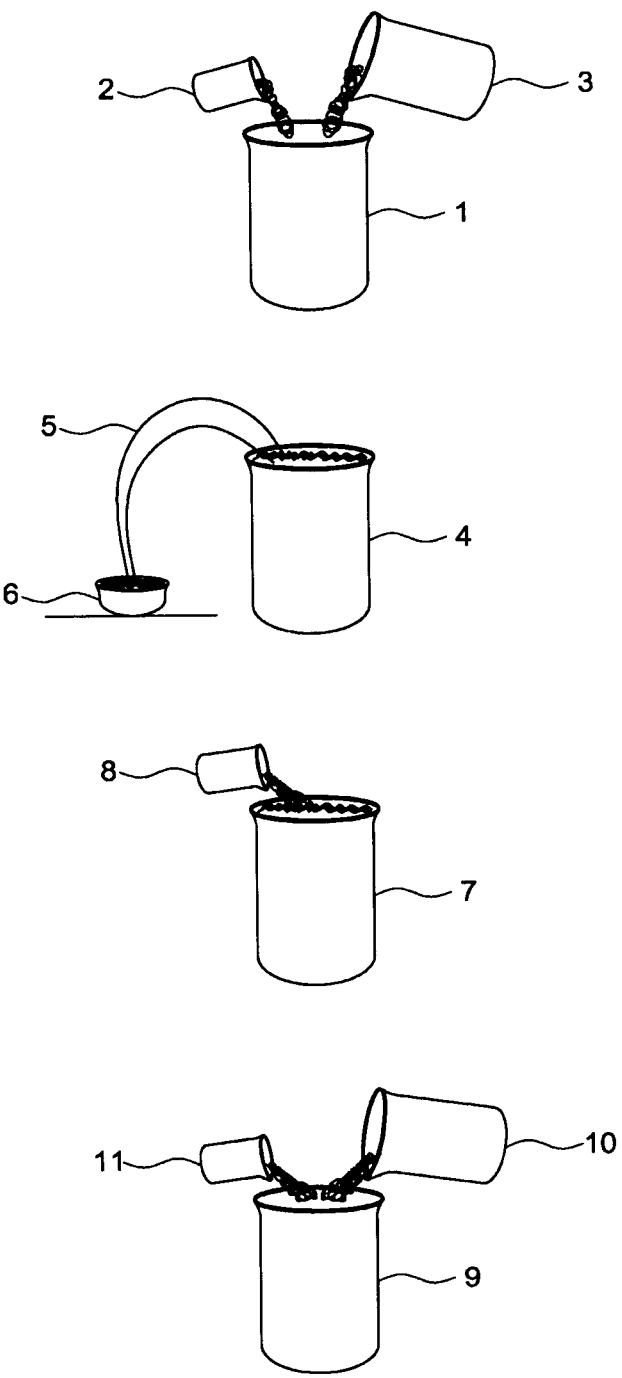
FIG. 6 shows the manufacturing process in which active and inert components are mixed, 1; a portion is removed, 4; and a portion is added, 7, in a "portion-removal/reconstitution process.

The process shown in FIG. 6 permits successive doses to be produced that differ by 0.0025 mg/100 mg tablet. FIG. 6 shows the same vessel in 1, 4, and 7 at different stages in a sequential process. In this manufacturing process specified proportions of buprenorphine 2 and inert 3 ingredients of filler/binder/diluent are added together and mixed in a vessel 1. The vessel in 4 represents 1 after mixing. A precise amount of the mixture in 4 is shown being removed via 5 into container 6. The exact composition of the removed portion 6 is known and doses are manufactured from this material. In 7 a precise amount of inert filler/binder/diluent is added, creating a mixture with an exactly known composition such that a successive batch of doses can be made, via the process shown of a precise amount of the mixture in 4 being removed via 5 into container 6 and then manufactured into doses. This protocol of removing an exact fixed amount and then adding an exact fixed amount permits a form of very tightly controlled dilution resulting in the capacity to manufacture doses differing by as little as 0.0025 mg per 100 mg from the previous batch. This protocol of 4, removing a precise amount, and 7 adding inert filler/binder/diluent is repeated until the entire series of doses required, having in the range of 2 mg/100 mg to 0.0025 mg/100 mg, is created with precision. Referenced and described in detail in Specifications and Claims as "portion-removal/reconstitution." In 9, inert filler/binder/diluent 10 is mixed with buprenorphine 11 in a more traditional process in which by mixing known quantities of each, in a series of procedures, each of which starts with new batches, as opposed to "portion-removal/reconstitution", doses of varying strength can be made. The process comprising 1, 4, and 7 allows for making the successive doses that differ by 0.0025 or 0.0050 mg/100 mg, as required by the opioid taper regimen.

Figure 7:
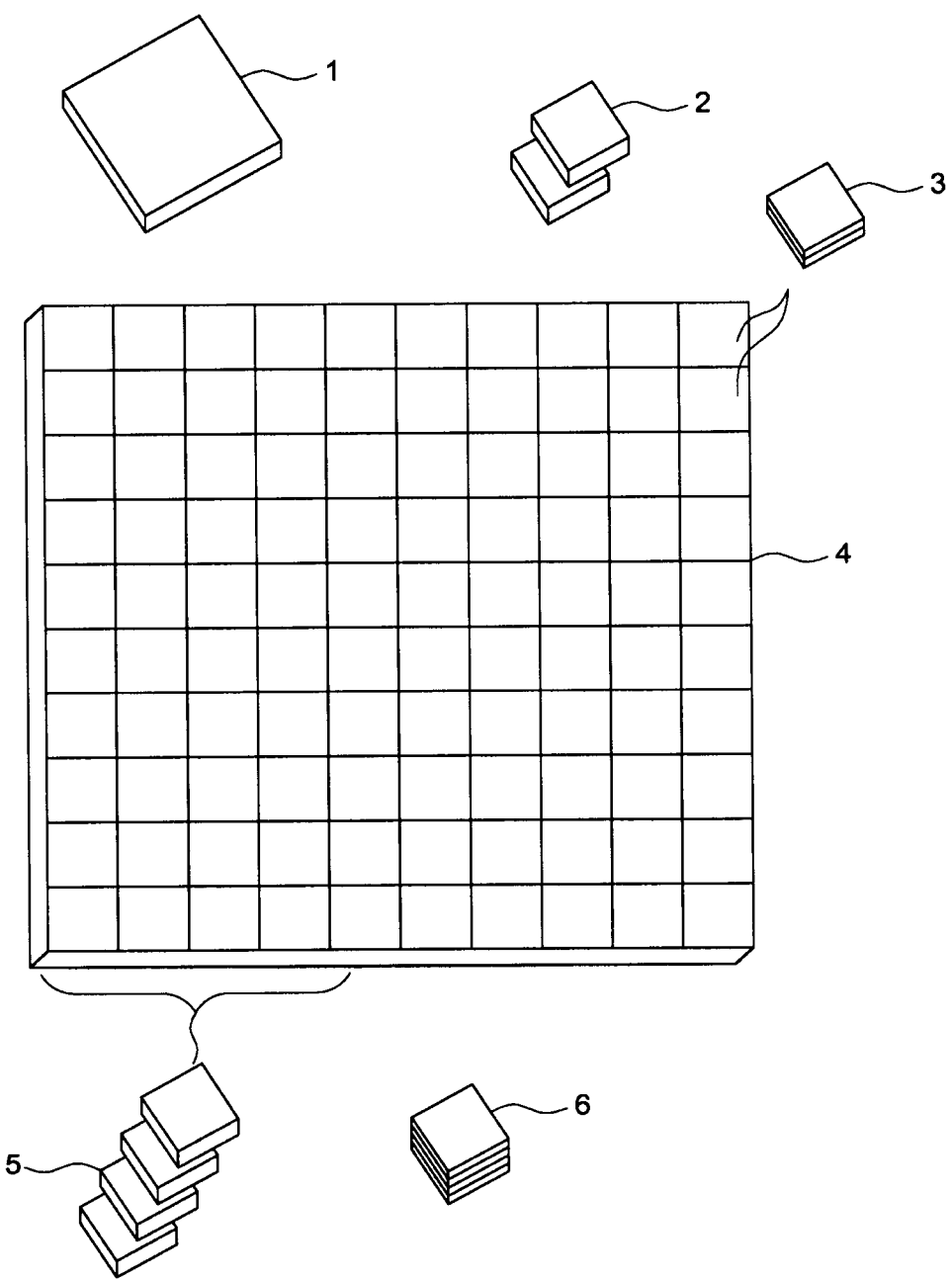
FIG. 7 shows a film, 1 and 4, containing buprenorphine in a completely uniform matrix and the lines along which it may be cut 4. Two examples, 2,3 and 5,6, are shown how pieces are recombined to form very small milligram amounts in exact doses.

FIG. 7 with 1 and 4 representing the same sheet of film suitable for sublingual or buccal medication delivery, with 4 being an exploded view of 1. The film of 1 and 4 is of uniform thickness containing buprenorphine in a completely uniform homogenous matrix as regards concentration of buprenorphine per volume of film. The lines in 4 show where the film is to be precisely cut into 100 pieces or a number of pieces of manufacturer's choice as regards quantity, shape and size. Due to uniformity of the film material, the exact amount in each piece is controlled via precision cutting. Pieces are combined to form exact doses, e.g., 2 identifies two pieces, each ¹⁄₁₀ of original sheet; 3 shows the pieces of 2 compressed. 5 identifies four pieces cut from the original sheet, each containing ¹⁄₁₀₀ of original sheet 4; 6 shows the four pieces of 5 compressed. Using this method, doses that differ by very small amounts, such as differences of 0.0025 mg per dose, are manufactured with the precision required by said opioid taper regimen of said invention. Specifications provides quantitative examples.

FIG. 8 is a table showing the dosage quantities of an opioid taper using buprenorphine. The table shows weeks 5 through 104 of a 118-week taper.

1 is the column showing the week number of the 7-day week of the taper.

2 is the total daily dose for each day in the respective week.

3 is the amount of each of the four times a day doses, i.e., one dose every six hours.

As is shown, the each week from 5 through 104 inclusive, once a week, the daily dose decreases by 0.02 mg of buprenorphine. Each 4 times per day dose decreases during these weeks by 0.005 mg of buprenorphine.

Prior to week 5 of FIG. 8, there are four weeks at the same dose as week 5. Weeks 105 through 118 are described in detail in Specifications, consisting of a dose lower than week 104 for ten weeks followed by four weeks of open label inert doses.

FIGS. 9A and 9B comprise a table showing the dosage quantities of an opioid taper using buprenorphine. The table shows weeks 5 through 204 of a 218-week taper.

1 is the column showing the week number of the 7-day week of the taper.

2 is the total daily dose for each day in the respective week.

3 is the amount of each of the four times a day doses, i.e., one dose every six hours.

As is shown, the each week from 5 through 204 inclusive, once a week, the daily dose decreases by 0.01 mg of buprenorphine. Each 4 times per day dose decreases during these weeks by 0.0025 mg of buprenorphine. Prior to week 5 of FIG. 8, there are four weeks at the same dose as week 5. Weeks 105 through 118 are described in detail in Specifications, consisting of a dose lower than week 104 for ten weeks followed by four weeks of open label inert doses.

DETAILED DESCRIPTION OF THE INVENTION

The following description is not to be taken in a limiting sense, but is made merely for the purpose of describing the general principles of exemplary embodiments, many additional embodiments of this invention are possible. It is understood that no limitation of the scope of the invention is thereby intended. The scope of the disclosure should be determined with reference to the Claims. Reference throughout this specification to "one embodiment," "an embodiment," or similar language means that a particular feature, structure, or characteristic that is described in connection with the embodiment is included in at least one embodiment of the present disclosure. Thus, appearances of the phrases "in one embodiment," "in an embodiment," and similar language throughout this specification may, but do not necessarily, all refer to the same embodiment.

Further, the described features, structures, or characteristics of the present disclosure may be combined in any suitable manner in one or more embodiments. In the Detailed Description, numerous specific details are provided for a thorough understanding of embodiments of the disclosure. One skilled in the relevant art will recognize, however, that the embodiments of the present disclosure can be practiced without one or more of the specific details, or with other methods, components, materials, and so forth. In other instances, well-known structures, materials, or operations are not shown or described in detail to avoid obscuring aspects of the present disclosure. Any alterations and further modifications in the illustrated devices, and such further application of the principles of the invention as illustrated herein are contemplated as would normally occur to one skilled in the art to which the invention relates. Unless otherwise indicated, the drawings are intended to be read (e.g., arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate. Also, as used herein, terms such as "positioned on" or "supported on" mean positioned or supported on but not necessarily in direct contact with the surface.

The phrases "at least one," "one or more," and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. The terms "a" or "an" entity refers to one or more of that entity. As such, the terms "a" (or "an"), "one or more" and "at least one" can be used interchangeably herein. It is also to be noted that the terms "comprising," "including," and "having" can be used interchangeably.

Further, all numbers expressing dimensions, physical characteristics, and so forth, used in the specification and claims are to be understood as being modified in all instances by the term "about", with the exception that milligram amounts are meant to be precise and within the limits permitted by mechanical measurement, formulation or determination. Accordingly, unless indicated to the contrary, the numerical values set forth in the following specification and claims can vary depending upon the desired properties sought to be obtained by the practice of the invention, with the exception that decreasing doses are meant to be as precise as methods permit their fabrication. At the very least, and not as an attempt to limit the application of the doctrine of equivalents to the scope of the claims; each numerical parameter should at least be construed in light of the number of reported significant digits and by applying ordinary rounding techniques, except when precision doses are presented. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 1 to 6.3, or 5.5 to 10, or 2.7 to 6.1.

For the purposes of promoting an understanding of the principles of the present invention, reference will now be made to the embodiments illustrated in the drawings and specific language will be used to describe the same.

Information as herein shown and described in detail is fully capable of attaining the above-described object of the present disclosure, the presently preferred embodiment of the present disclosure; and is, thus, representative of the subject matter; which is broadly contemplated by the present disclosure. The scope of the present disclosure fully encompasses other embodiments which may become obvious to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims.

Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail may be made, without departing from the spirit and scope of the present disclosure, as set forth in the appended claims, as may be apparent to those of ordinary skill in the art, are also encompassed by the present disclosure.

Medications combined with other medications such as, buprenorphine combined with naloxone or hydrocodone combined with acetaminophen shall be computed based on the opioid component and shall be considered, for purposes of this invention, to be the amount of opioid present. These opioids are claimed as equivalents, as when used as per standard morphine equivalent conversion charts: buprenorphine patch or film; butorphanol; codeine; dihydrocodeine; fentanyl buccal or SL tablets, or lozenge/troche; fentanyl film or oral spray; fentanyl nasal spray; fentanyl patch; hydrocodone; hydromorphone; levorphanol tartrate; meperidine hydrochloride; methadone; morphine; nalbuphine; opium; oxycodone; oxymorphone; pentazocine; tapentadol, and; tramadol.

The present invention, an opioid taper regimen kit is a medication-based treatment designed for use with patients who are diagnosed with opioid dependency, opioid addiction, opioid use disorder and similar or related conditions in which dependency upon opioids is a central component. The invention uses an opioid medication, in decreasing doses over time, to allow the patient to move to zero use of opioid. The scheduled doses are determined prior to the start of treatment with timeframes of dose reduction differing, dependent upon starting dose and amount of dose-reduction per week. This invention addresses the issue of creating appropriate dosage reduction increments to avoid withdrawal symptoms at very low doses, as described. This invention solves the problem of creating what are doses that are small enough for a smooth taper (i.e., a taper slow enough so as to not generate significant withdrawal symptoms) and to avoid the dosing inaccuracies that are created by informal cutting of medication films by patients and the challenges to most patients of dividing tablets that are not intended to be divided, to a milligram, or sub-milligram, level. These are two barriers encountered by the clinician and the patient who are devising a withdrawal regimens in which it becomes apparent that downward dosage increments are need that are smaller than commercially available.

Doses decrease in a linear manner for more at 99%, or more, of the reduction steps of the duration of the regimens and are not based on a percentage of a previous dose. Said invention consists of a series of scheduled decreasing doses over a period of years. "Scheduled" here means, in part, that prior to an individual starting a regimen each dose over the period of the regimen is identified as to amount and time interval from previous dose. "Scheduled" also means that a specific regimen is used for all persons starting that regimen. The regimen is packaged in a series of blister packs, each blister pack, on a card, designated for a specific week, over a period of two to four years, or more, relative to specific regimen prescribed. All 28 doses in a given week are at the same dosage level as every other dose in a given week, for every week of every regimen. Dose reduction, is always once every seven days, except for a period of weeks at the end at 0.001 milligram (mg)/day in four divided doses.

A pre-scheduled regimen stands in contrast to most current treatments of opioid disorders in which there is usually frequent adjustment to dosage levels that are made when the patient and the prescribing clinician confer. Such patient/clinician appointments are often on a monthly basis, once medication assisted treatment (MAT) is underway.

A "taper" of a medication refers to the reduction of that medication over time. The present invention is an opioid taper kit. Two specific examples described herein of the invention in the range of doses and times described, comprised of medication administered over a period of time in a range of 118 to 218 weeks. As indicated, with dosage starting points above 2.0 mg/day of buprenorphine, or its equivalent, treatment times will extend further, such as 418 weeks or 818 weeks for 3 and 4 mg starting points. These time periods far exceed any previously described opioid-to-abstinence treatments, often by an order of magnitude. This range can be adjusted using the approach described herein by selecting the rate at which the patient can tolerate withdrawal, i.e., 0.01 or 0.02 mg buprenorphine per week.

Recent advances in the understanding of the pharmacology of other addictive medication, SSRIs, lend support to the structure of this invention. (Horowitz)] Said invention is designed such that dose reductions are small enough not to require a pause in the incremental step reduction regimen at any specific week. The design is such that the prescribing clinician can pause the reduction schedule by prescribing the same dose for as many weeks in a row as deemed necessary.

Two embodiments of the many possible within the ranges described, are presented herein: A 118-week and a 218-week version. If a patient is started on the 118-week version and showing a degree of withdrawal that cannot be tolerated or cannot be maintained, the patient may be changed to the 218-week regimen, which tapers at one-half the rate of the 118-week regimen, i.e., a reduction of 0.01 (one one-hundredth) of a milligram per week for 200 of the 218 weeks vs the reduction of 0.02 (two one-hundredths) of a milligram per week for 100 weeks of the 118 week regimen.

Said present invention is intended as appropriate treatment for patients who are in an adequately supervised clinical program, predominantly for out-patient, but also appropriate in some aspects of residential treatment. Said invention is designed for use with individuals who have stabilized at a relatively low dose of opioid. "Relatively low" dose here being somewhere approximately in the range of 2.0 (two) to 4.0 (four) milligrams (mg) per day of buprenorphine. Below 1 mg/day total may be considered "very low." If a patient is stable at one milligram of buprenorphine/day, or equivalent, or less, the patient may be started at that dose. Said invention is also designed for individuals that have recently moved to buprenorphine from other opioids. The present invention is intended for patients who are maintained at the same dose in the 2 to 4 mg range for at least four weeks without the emergence of significant withdrawal symptoms.

The detailed description herein is specifically for stabilized patients starting at 2 mg/day buprenorphine and utilizing a 118-week or 218-week regimen. As noted, the principles described herein, for 0.01 mg or 0.02 mg of buprenorphine per week reductions, and the relevant principles of manufacture, may be applied to individuals starting at doses higher or lower than 2 mg/day total.

There are several novel concepts incorporated into the present invention. One novel aspect is rate of reduction of the opioid medication. The linear rate of reduction of dosages is equal to being in the range of 0.01 (one one-hundredth) mg to 0.02 (two one-hundredth) of a milligram every seven days, i.e., once a week. Linear reduction stands in contrast to regimens that recommend continually reducing by a percentage of a recent previous dosage level.

In said invention's manufactured treatment kit embodiment, an individual at 2.0 mg/day of buprenorphine, in four divided doses, is provided 2.0 mg/day, for four weeks, to assure stabilization. "Stabilization" herein means that withdrawal symptoms are not leading to a desire for an increased dosage regimen. The one hundred weeks of 0.02 mg reduction occurs within a 118-week period. After the four weeks of stabilization, the dose, in this invention, is reduced, in the 118-week embodiment herein described, by 0.02 (two one-hundredths) of a milligram per week to 1.98 mg/day, in four divided doses of 0.495 mg each, once every six hours, i.e., q.i.d. The dose is 1.98 mg/day for seven days. This reduction of 0.02 mg per week is maintained for 100 weeks, under conventional clinical supervision.

In the 218-week regimen described, within the broader range mentioned, there is a 0.01 (one one-hundredth) mg per week reduction. This is a reduction at half the rate of the 118-week reduction. 118-weeks and 218-weeks reference the overall time of the regimen. The two hundred weeks of 0.01 mg reduction occurs within the 218-week period. The dose diminishes from the initial stabilized dose of 2.000 mg/day, in four divided doses of 0.500 mg q.i.d, for four weeks. At the start of the fifth week, the daily total goes to 1.99 mg/day for a week, in four divided doses of 0.4975 mg buprenorphine, q.i.d. The subsequent reductions in this 218-week regimen are each at the interval of 0.01 (one one-hundredth) mg reduction per week. The challenges posed to precision manufacturing, and solutions to the challenges, are discussed below.

No published or promulgated or discussed linear opioid taper has described a taper as slow as 0.01 mg/week or 0.02 mg/week for this protracted period of time, nor any time close to this magnitude of time. "Linear" here means that the amount of dose reduction per unit of time is the same. There are some exponential reduction regimens that, at certain points, could theoretically be in the same range of dose reduction for a relatively brief period of days, if those points were ever reached in exponential reduction formats of reduction, assuming such protocols have been carried out. The detail, i.e., exact dose to thousandths of a milligram, of every dose during 118-week and 218-week periods is provided in tables in this application, FIGS. 8, 9A and 9B.

No credible example of a regimen has been found that demonstrates achieving abstinence in any significant percentage of participants. This invention utilizes a timeframe that is orders of magnitude longer than previous attempts found in the literature and dose reductions than are smaller, usually by at least an order of magnitude, than any previous protocol found in the literature.

Novel aspects are that this regimen of a scheduled, manufactured, packaged series of slowly reducing medication doses. This invention has not existed previously, nor does it exist elsewhere as a description nor as a product at this time. There are some products that manufacture dosages at different levels however, the increments between the doses are significantly larger and instructions caution against dividing the doses. One product on the market has 150 microgram (0.15 milligram) steps and recommends dosing every 12 hours. These steps are about 7 to 15 times the size of said invention and dosing is at twice the interval. Compared to the 0.01 weekly reductions herein at six hours, the rate of reduction would be about 30 times as great. Said invention thereby represents an advance for individuals too sensitive to relatively large dosage drops, particularly when coupled with a method of manufacture that permits such small dosage differences to be made and packaged.

Another novel aspect of the present invention is that the daily dose is divided into 4 (four) doses per day. While many medications are taken four times/day, i.e., q.i.d., it is not found in prior opioid reduction regimens, except perhaps in some experimental stabilization regimens that use q.i.d. dosing for stabilization but not for treatment. In the present invention, whenever the active ingredient is present, the patient is taking their daily dose in four divided doses, one dose every six hours.

The effective half-life of buprenorphine can vary from one patient to another. Additionally, buprenorphine half-life can be affected by an individual's metabolic rate, diet, stress, illness, co-morbidities, and the concurrent use of other medications, for example. One commonly used metric for buprenorphine half-life is 37 (thirty-seven) hours. A half-life calculation finds that available buprenorphine in a patient's system, after six hours from the peak of the last dose is about 89 (eighty-nine) percent, not accounting for any residual from prior doses. A number of regimens that use percentage reductions consider ten percent to be about the maximum dose reduction permissible before expecting withdrawal symptoms to occur at a level that may encourage regression. When a patient regresses, said patient may feel so uncomfortable as to feel compelled to take more than their prescribed dose of opioid or to accelerate their schedule of doses. From the perspective of this invention, a protracted ten percent reduction in available opioid, is accepted as causing cravings and symptoms of withdrawals in significant numbers of individuals and this is reflected in the structure of the invention, i.e., doses q.i.d. The time to reach a ten % reduction of available opioid will vary from patient to patient but likely starts around six hours for significant numbers of individuals, based on the generally accepted half-life and half-life calculators.

Manufacture:

Other than methods specified below herein for achieving dose precision within the examples of the 118-week or 218-week kits, manufacture utilizes the standard, established, accepted and proven pharmaceutical manufacture methods for creating doses, such as tablets (or films or patches), packaging the tablets in blister packs, providing appropriate labels and inserts, and boxing in correctly labeled boxes. These accepted methods include adherence to all regulations governing pharmaceutical manufacture. The detailed descriptions of 118 and 218 week regimens and their manufacture are examples of regimens that fall within the range described. By changing the precise amount of reduction or the starting point, or the exact number of days at each dosage of medication, there are an almost infinite number of configurations. The basic concept of two-plus years and the micro-reductions described herein, plus the q.i.d. dosing throughout, coupled with 5 to 15 weeks near the end of 0.01 mg buprenorphine followed by four weeks of various placebos remains novel and nonobvious. The specific 118- and 218-week regimens as representative starting points of desired opioid use reduction, i.e., 2 mg/day of buprenorphine, and are dosage levels at which problems with opioid reduction often occur. The examples utilize taper amounts designed to be effective with a large number of addicted/dependent individuals, i.e., 0.01 and 0.02 mg/week reduction of buprenorphine and to overcome the most common reason for patients to interrupt an attempt at withdrawal, namely, the emergence of withdrawal symptoms that exceed the patient's ability to continue with a reduction regimen.

The overall appearance of each week's medication blister pack is the same in the examples provided, except weeks 116-118 and 216-218, as described: Each week, comprises a blister pack of 28 doses. Each dose in a given week has the same quantity of medication as every other dose in that week. The following three weeks do not contain 28 doses of active ingredient and instead contain the indicated number of inert doses: Weeks 116 or 217: three doses per day inert matter, i.e., blister pack card for a week contains 21 inert doses; Week 117 or 217: two inert doses per day, with 14 doses per weekly card; Week 118 or 218 with seven inert doses/card. Content of medication for weeks 116-118 or 216-218 explained below.

Dose labeling as per regulations: Each different dose bears a unique identifier. Tablets of different strengths bear different imprinted codes to permit medication identification. Medication cards (blister packs) and foil wrappers of film are also labeled as to medication and dosage.

One aspect of the novelty and non-obvious elements are in the amount 0.01 or 0.02 mg reduction (weeks 5-214 and weeks 5-114) in 218- and 118-week regimens, respectively, of dose progression. Also novel is the 0.0025 or 0.0050 mg interval, and the range of 0.0010 to 0.0100 mg between successive doses and the specificity with which each dose in the 118 or 218-week regimen is described and embodied to the thousandth of a mg. The manner of manufacturing the finished product in the range of 118-weeks to 218-weeks of blister packs, is described below.

Parameters of the Regimen:

First four weeks of the 118-week regimen: Each dosage level for the first four weeks is the same in each of the four tablets taken every six hours, i.e., q.i.d., and are manufactured to be 0.500 mg buprenorphine each. Four doses per day total 2.000 (two) mg per day buprenorphine. Three possible methods of manufacturing doses to this level of precision, such that, for example, doses consistently separated by 0.0025 mg, for example doses of 0.4950 mg and 0.4925 mg can be manufactured, are described below and such methods are used to produce the described doses. One reason no protocol exists with dose reduction steps this small is likely that the method to economically produce medication with acceptable tolerances of intervals this small, apparently has not been described. Although techniques have been developed that permit micro-doses to be loaded into capsules, it does not appear that the tolerances could be achieved to consistently produce, on any level dictated by production economics, one capsule with, for example, 0.4950 mg and another with 0.4975 mg and so on through a series that differs by 0.0025 mg from one dose to the next (Bi et al). Dilution is an established component of pharmaceutical production. Dilution with the herein described methodology, of "portion-removal/reconstitution", for the purposes of manufacturing a gradated series of steps for the purpose of opioid dose reduction is not found in literature. Methods to achieve this precision are part of this invention, as described below.

Following four weeks of stabilization at a manufactured 2 mg/day total dose, i.e., 0.500 mg, q.i.d., then weeks 5 through 104 (100 weeks) in the 118-week regimen are manufactured to start in week five (i.e., days 29 through 35) at 0.495 mg four times a day at six-hour intervals for a daily total dose of 1.980 mg/day. As noted, each of the 28 tablets every week of this regime are the same as each of the other tablets of that specific week.

Manufacture of weeks 5 through 104 creates a linearly decreasing series of doses from one week to the next. In the 118-week regimen, there is a series of 100 weeks during which, at the end of each week, the daily total dose decreases by 0.02 (two one-hundredths) mg. This is reflected in each of the four divided doses, i.e., every six hours, each of the four daily doses decreasing per week by 0.005 mg of buprenorphine. Subtraction, through use of the specified manufacturing process below, of 0.005 mg, ninety-nine times, from a starting dose of 0.500 mg will result in doses for week #104, each containing 0.005 mg buprenorphine for a 0.02 mg daily total of buprenorphine., when the 0.005 mg dose is q.i.d.

Weeks 105 through 114: The 4-a-day tablets (every six hours) manufactured for the ten weeks of week 105 through week 114 each contain 0.0025 mg of buprenorphine. This provides a daily total dose of 0.01 (one one-hundredth) mg buprenorphine (equivalent in pain reduction effect to 0.3 (three-tenths) mg morphine) (Center for Medicare and Medicaid Coverage). This of 0.01 (one one-hundredth) mg is lower than the dose that many clinicians would consider capable of normally having any effect pain reduction effect and is intended rather to reduce the possibility of withdrawal symptoms. As before, every q.i.d. dose during the ten weeks 105-114 is manufactured to be the same 0.0025 mg of buprenorphine as every other dose in the 280 doses consumed in this 10-week period. The patient is consuming a total of 0.07 mg of buprenorphine per week. In the ten-week period, 0.7 mg of buprenorphine are consumed, equal in equivalency charts to 2.1 mg morphine per week, or 21 (twenty-one) mg of morphine in the ten weeks.

Weeks 105 through 114 represent a 50 (fifty) percent reduction over week 104 by going from 0.02 mg per day to 0.01 mg per day and is the first and only time in 100 weeks that the reduction is not a linear 0.02 mg of buprenorphine reduction. Considering the 101 (one hundred and one) reductions in the same number of weeks, with 100 of them being linear, this means that of the 101 reductions, in the 118-week regimen, 100 weeks have a linear reduction, that is, more than 99% a linear series of reductions and may be considered as essentially linear, except for the next-to-last step down, from 0.02 to 0.01 mg/day total and then for the final step to zero mg/day.

Weeks 115 through 118: These doses are known by clinician and patient to contain no active ingredient, this being an open label, doubly unblinded, pharmacologically inactive, tablet. The inert doses have the same appearance as previous doses in the regimen, in every aspect, except the ID code on the tablet. Manufacture is such that these doses contain no active ingredient but contain the same inactive ingredients with a total weight the same as all previous doses in the regimen.

It is well-accepted in addiction medicine that part of the induced physiology of addiction is related to the psychology of setting and repeated ritual. This four-week component of with no active ingredient is designed to wean the patient from the ritual of drug-taking. Most patients have long histories of opioid use prior to treatment. The ritual with no active ingredient substitutes for the ritual of many years of drug use with an active ingredient and is designed to help with the final withdrawal from opioid medication. Each successive week of weeks 115 through 118 reduces the number of daily doses by one, i.e., q.i.d., then t.i.d., then b.i.d., and in the final week, q.d., as described below. Detail of the final four weeks follows here:

Week 115: Four inactive doses/day. Each blister pack is manufactured to be comprised of 28 blisters on a blister pack, each containing an identical inert dose with no active ingredient. These are taken every six hours, i.e., q.i.d.

Week 116: Three inert doses/day. Each blister pack is comprised of 21 blisters each containing a dose with no active ingredient on a card/blister pack. These are taken every eight hours, i.e., t.i.d.

Week 117: Two inactive doses/day. Each blister pack is comprised of 14 blisters on a card/blister pack, each blister containing a dose/tablet with no active ingredient. These are taken every 12 (twelve) hours, i.e., b.i.d.

Week 118: One inactive dose/day. Each blister pack is manufactured to be comprised of the 7 (seven) blisters on a card/blister pack, each containing a dose/tablet with no active ingredient. These are taken once every 24 hours, i.e., once a day, q.d.

Dispensing of a 28-day supply of buprenorphine or buprenorphine/naloxone is the norm. Under current guidelines, four of the above manufactured blister packs are packaged together, as per illustrations, comprising four weeks of medication, i.e., four blister packs of 28 tablets each (except weeks 116-118, which contain blister packs with 21, 14 and 7 doses) in a box.

Manufacture assures that the largest font on each blister pack card is the number of the week, e.g., Week 56. This week number labeling is on each daily tear-off tab, as described herein, designed to be easily readable by a patient. Clear numerical labeling aims to avoid confusion upon opening a monthly box as regards correct, and critically significant, sequence of use of enclosed blister packs which clearly show, e.g., Week #26, Week #27, Week #28, Week #29 and so on from Week #1 to Week #118 or whatever end week may be in a specific regimen. Clinicians are provided sample boxes with cardboard cards printed to look like blister packs, designed to permit demonstration re taking doses in the succession indicated by the week number, as this is central to the regimen. There is a highly visible card in each package that is devoted solely to instructions for correct use of blister packs in succession. The card describes in 25 words or less, in 16 point font, or larger, the sequence in which medication must be taken.

As noted above, manufacture of the 118- or 218-week kits, or any kits in or outside this general range of weeks, utilizes standardized and proven pharmaceutical manufacture methods for creating tablets, packaging the tablets in blister packs, providing appropriate labels and inserts, and boxing in per regulations. Methods for achieving dose precision are described following the embodiment of the 218 regimen, directly below for the scheduled opioid regimen taper.

The immediately above describes embodiment of the 118-week regimen. The embodiment of the 218-week regimen is described immediately below. The principles are the same. The major difference is that the weekly steps in the 218-week regimen are a decrease of 0.01 mg each week, whereas in the 118-week regimen, dosage decreases are twice that magnitude, at 0.02 mg/week buprenorphine.

The overall appearance of each week's medication blister pack on weeks 1 through 218 is the same (except for weeks 216-218) and has the same general appearance, except labeling and distinguishing color of blister pack: There is a blister pack of 28 doses, that is four doses per day; each of the 28 doses in a given week has the same quantity of medication as the other 27 doses in that week.

The first four weeks of 218-week regimen are the same as first four weeks of the 118-week regimen, or any regimen in the ranges specified herein: Each dosage level for the first four weeks is the same in each of the four tablets taken every six hours (q.i.d.), and are manufactured to each be 0.500 mg buprenorphine. Each of the 112 tablets taken during the first four weeks (28 days) is the same dose, 0.500 mg, as the other 111 tablets. Three possible methods of manufacturing such a dose are described below.

The 118-week regimen, when starting at 2.000 mg/day of buprenorphine, reduces by 0.02 mg buprenorphine per week for weeks 5 (five) through 114 (one hundred and fourteen). The 218-week regimen, starting at 2.000 mg/day, also for four weeks, in divided doses, reduces the dose by 0.01 mg per week, each week, starting with week 5 (five) through week 214 (two-hundred and fourteen), that is, a reduction of 0.01 mg/week, each week for 200 weeks. The rate of reduction in the 218-week regimen is therefore, for the 200 (two hundred) significant dose-reduction weeks, is half the rate of reduction of the 0.02 mg per week reduction of the 100 weeks of the 118-week regimen. The 218-week regimen is intended for patients, as determined by their provider, deemed too sensitive to withdrawal symptoms for a 0.02 mg/week reduction or who fail while attempting the 0.02 mg/week reduction of the 118-week regimen. Much of current thinking in the field would tend to reject a 0.01 mg/buprenorphine/week reduction as unnecessarily small. This thinking appears to have contributed to the lack of efficacy of essentially all previous taper trials.

Weeks 5 through 204 (200 weeks) in the 218-week regimen are manufactured (details below) to start in week five (i.e., days 29 through 35) at 0.4975 mg four times a day at six-hour intervals for a daily total dose of 1.9900 mg/day. See below for a manufacturing technique that permits this degree of precision. Each of the 28 tablets of week number five week are of the same dose.

Manufacture of weeks 5 through 204 produces a steadily, linearly decreasing, dose from one week to the next. In the 218-week regimen, there is a series of 200 weeks during which, after the last dose of each week, the daily total dose decreases by 0.010 mg. This is reflected in that the four divided, every-six-hour, doses each decrease weekly by 0.0025 mg of buprenorphine. Reduction, through the manufacturing process, of 0.010 mg one hundred and ninety-nine times, from a starting dose of 2.000 (two) mg will result in the 28 doses for week 204, each q.i.d. dose containing 0.0025 mg buprenorphine for a total of 0.01 mg daily (24-hour period) of buprenorphine.

Weeks 205 through 214: The 4-a-day tablets manufactured for the ten weeks 205 through weeks 214 each contain 0.0025 mg of buprenorphine. This is the same level of medication as weeks 105-114 in the 118-week regimen. This provides a daily total dose of 0.01 mg buprenorphine which is often regarded as equivalent in pain reduction effect to 0.30 mg morphine. As noted, this is lower than the dose that many clinicians would consider capable of normally having any pharmacological effect, as regards pain reduction or prevention/avoidance of withdrawal symptoms. Herein, it is included, being believed to be therapeutic and necessary. As in the 118-week regimen, every q.i.d. dose during the ten weeks 205-214 is manufactured to be the same 0.0025 mg of buprenorphine as every other dose in the 280 doses consumed in this 10-week period. As with the 118-week regimen in the last ten weeks of active ingredient dosing, the cumulative dosing is 0.07 (seven-tenths) mg of buprenorphine/week (MME 2.1 mg of morphine/week). The patient is consuming a total of 0.7 mg of buprenorphine in a ten-week period, equivalent to about 21 mg of morphine per 10 weeks. The 30 to 1 equivalency, buprenorphine to morphine, is used herein to provide a quantitative comparison with a pain medication that has been available for nearly 200 years, i.e., morphine, and for which many clinicians have a better developed prescriptive and experiential familiarity as compared with buprenorphine.

Note that weeks 205 through 214 (in the 218-week regimen) represent a continuation of week 204 and is the first time in 200 weeks there is no dose reduction. In other words, Week 204 is 0.01 total per day buprenorphine and so are the following ten weeks. Considering the 200 (two hundred) reductions in the same number of weeks, this means that the regimen is more than 99% a linear series of reductions and may be considered as essentially linear, except for the last step down, which is of the said additional 10 (ten) weeks duration past the usual one week (#214) at a new dosage level at 0.01 total daily buprenorphine.

Weeks 215 through 218: The doses during these four weeks are known by clinician and patient to contain no active ingredient. As with the last four weeks of the 118-week regimen, this is an open label, doubly unblinded, pharmacologically inactive, tablet. These doses look the same in every aspect, except the code on the tablet. Manufacture is such that these doses contain no active ingredient but contain the same inactive ingredients with a total weight per tablet the same as all previous doses in the regimen. It is well-accepted that part of many addictions is stimulation due to setting and perception of drugs or drug paraphernalia and that often drug-seeking behavior results in repeated ritual as part of the effort to reduce withdrawal symptoms. This four-week component and rationale is described above as the last four weeks of the 118-week regimen.

Weeks 215 to 218 are the same as weeks 115 through 118 in the 118-week regimen, as described above. See above for comments on dispensing, labeling and packaging. Every week's, 28-dose card in the 118-week and 218-week series has tear-off tabs for each day. This allows a patient to carry only a few tablets at a time and reduces the possibility of loss of a week's medication while still allowing for strong visual and physical cues from the blister package for what medication has been consumed and what remains to be consumed.

Manner of Manufacture— as regards the specification of the manner and process of making the invention: The present invention is manufactured using specific approaches detailed below, of mixing ingredients to create unique dosage amounts. In addition to using the specific method described, standard and well-established pharmaceutical methods are employed in order to: Form adequately durable medication doses, such as tablets, lozenges, sprays, liquids or films, and to package doses in appropriate packages for durable storage. Where the invention differs from past products is in the unique process for creating doses that differ in a precision amount at very low and in creating a nonobvious treatment regimen that is packaged for use. The doses and dosing intervals are novel and nonobvious, going against much conventional thinking about sensitivity to incremental dosage reduction, and to the extent that standardized processes are used to make a novel and nonobvious product, there is novelty and nonobviousness in the finished product due to in uniqueness of the dosing regimen.

A central aspect of manufacture addresses the precision required in manufacture of doses that are very close in weight, e.g., in a range of 0.0010 to 0.0070, from one week to the next, as regards quantity of medication per dose, with specific examples herein of weekly reductions of 0.0025 and 0.0050 mg, which are then sustained for seven days. In these regimens, acknowledging the degree of patient sensitivity to dose reduction is essential to understanding the rationale for the precision described herein. The sensitivity to dose reduction is understood here to be significantly greater than what has previously be the general understanding of sensitivity to dose reductions in previously attempted regimens. Addressing this level of sensitivity to dose reduction is the key component of said invention.

Manufacture by precision dilution: A method to achieve dosage accuracy through portion-removal and reconstitution of a precisely composed initial lot of a pharmaceutical compound follows. "Portion-removal" here means that a portion of a batch medication compound is removed from the mixing vessel following reaching homogeneity endpoint. "Reconstitution" here means that the mass of the batch is restored to that prior to portion-removal. Reconstitution of mass in this process is always with inert filler/binder/diluent or industry equivalent. Moisture content is maintained sufficiently constant, or adequately monitored and compensated for, so as to not distort precision production through presence of $H_2O$ in compound or components. The following manufacture protocol produces doses that differ by 0.0025 mg of buprenorphine for use in q.i.d. dosing. The purpose of the manufacture protocol is to assure adequate precision of doses throughout the entire 118- or 218-week, or longer, regimen so that steps down do not produce withdrawal symptoms of sufficient strength to cause patient regression to higher doses or doses at a smaller time interval.

Herein described portion-removal and reconstitution of a batch will permit precision from dose to dose, whereas, starting with different initial batches of buprenorphine added to filler/binder would be more likely to introduce a lack of precision when decreasing from one weekly dose to the next weekly dose, if successive doses are made from different batches of buprenorphine. This is due to acceptable levels of variation in starting materials and finished products, under current regulatory guidelines. These guidelines would allow variability to exceed that which is required to produce successive weeks to the tolerances herein specified.

For example, if Week #50 were made from one batch of buprenorphine and Week #51 were made starting from another batch of buprenorphine, accurately controlling the 0.0025 difference needed would be less likely with traditional mixing methods, than with described portion-removal/reconstitution approach and the method herein is therefore an advance.

Portion-removal/reconstitution results in: 1) The portion removed in $1^{st}$ step has a known concentration from which doses can be manufactured, and 2) After the $2^{nd}$ step of adding a precise amount of filler/binder to said batch, the working batch is now diluted by a precise amount such that doses with an exact difference, compared with those doses made from the just previously removed portion, can be manufactured with high level of precision.

As described below, this assures, as an example, that one week differs from the next week by 0.0050 mg per dose in the 100-week uniform reduction phase of the 118-week regimen; and differs by 0.0025 mg from week to week in the 200-week uniform reduction phase of the 218-week regimen. In a q.i.d. regimen, these 0.0050 mg and 0.0025 mg differences per dose result in a reduction of 0.02 and 0.01 mg buprenorphine as a daily total, once each week.

Described portion-removal/reconstitution eliminates the issue of batch-to-batch purity of buprenorphine, or other active ingredient, in a protocol. By using the same lot of buprenorphine/inert components for the manufacture of an entire regimen (e.g. 118-218 weeks), and using described portion-removal/reconstitution, the manufacturing difference from one week to the next can be precisely controlled to be a consistent step down of 0.01 or 0.02 mg decrease per week, i.e. reduction of 0.0025 or 0.0050 q.i.d. respectively. This eliminates the need to compare week X dose concentration with week X+1 dose concentration manufactured from a different batch of buprenorphine. This is the result of every week being manufactured from a single batch having uniform purity. It does impose the limitation that a patient's entire regimen must come from one manufacturing batch, or risk differences from week-to-week. This has implications for manufacture and distribution to assure adequate reserves of each lot. For a patient starting again after a failed attempt to withdraw, if several weeks have passed, it will not be of significant what lot is used if dose is matched to current level of opioid use and there is a period of stabilization.

It may be possible to use different batches and traditional methods of mixing if a manufacturer is able to demonstrate adequate consistency from batch to batch through use of established quality control methods employing quantitative analysis. Because margin of error, week to week, is smaller than with most or all previous medication regimens, precise quantitative analytics will be needed to ensure adequate consistency from batch to batch, if portion-removal/reconstitution is not utilized.

The portion-removal/reconstitution method is described herein, as is the alternative approach of using varied starting batches of buprenorphine. Note regarding Morphine Milligram Equivalent (MME): A difference of 0.005 mg buprenorphine per q.i.d dose, that is, 0.02 mg buprenorphine total difference per day, equals 0.6 mg of morphine difference per day, when the dosage changes at the end of each week (seven days). A reduction of 0.01 mg of buprenorphine is equivalent to a reduction of 0.3 mg morphine per day (Centers for Medicare and Medicaid Services).

Method of Manufacture:

To utilize portion-removal/reconstitution: 1) Obtain adequate quantities of: A) buprenorphine of acceptable and known level of purity, and; B) pharmacologically inert filler/binder/diluent, or industry equivalent, with proven record of effective use with buprenorphine tablets, or comparable ingredients for production of other formats, such as film, patch or spray. If more than one batch of buprenorphine is used, the purity of the buprenorphine must be able to be duplicated from batch to batch, since patients are intended only to use medication from a specific batch throughout their two or four years (118-218 weeks) or more. Specialized storage protocols, e.g., temperature and humidity control or controlled atmospheric composition, or special packaging techniques or a combination of all these, by manufacturer or distributor will be required to maintain medications that are manufactured years prior to use in order to maintain strict batch control, such that their expiry date meets standards.

To start, manufacture the divided q.i.d. doses for the first four weeks of 118-week course (118 weeks includes 100 weeks of uniform dose reduction) of 2.00 mg buprenorphine per daily dose in four divided doses, which is 0.500 mg buprenorphine q.i.d. That is, each q.i.d. dose contains 0.500 mg buprenorphine. Specific amounts are indicated herein. If ratios of ingredients are maintained, any feasible batch size can be manufactured using other masses. This is done through following actions:

Action: Take 103.000 (one hundred and three) kilograms of a mixture consisting of: A) 0.515 (point five hundred and fifteen) kg of buprenorphine, and; B) 102.485 (one hundred and two point four eighty-five) kilograms of filler/binder/diluent, or calculated multiples of these masses.

Action: Mix ingredients until homogeneous, assaying if necessary, for homogeneity, with mixture showing presence of 0.500 (one-half) mg per 100.000 (one hundred) mg, i.e., equal to one part per 200 parts. Monitor and maintain $H_2O$ content of mixture, even if minimal, throughout entire following process such that there is no appreciable distortion due to moisture variations.

Action: Remove 4.000 (four) kilograms of the said 103 kg mixture, leaving 99 (ninety-nine) kg, consisting of (0.5% active)/(99.5%) inactive mixture. Use the removed portion of 4.000 (four) kilograms to make 40,000 doses/tablets of 100 mg, each dose/tablet containing 0.500 mg of buprenorphine. Although precisely 4 kg is removed, after processing this 4 kg into doses, there will be some slightly lesser number of doses produced due to residue in manufacturing equipment.

Action: Add precisely 1 (one) kilogram of the inert components (filler/binder/diluent) utilized to the above mass of 99 kilograms (the said 103 kg minus 4 kg) to reconstitute mass to 100 kg and mix to total homogeneity, assaying if needed, guarding against, and correcting for, moisture content variation. This reconstituted batch will contain the 0.495 kg of buprenorphine that remained in the 99 kg after 4 kg portion-removal. When reconstituted to 100 kg, the 0.495 kg in the mixture will yield 100 mg doses containing each containing 0.495 mg. Four of these q.i.d. doses equal 1.98 mg of buprenorphine total dose per day. This is equivalent to 59.4 mg morphine, accepting the 1 mg buprenorphine equal to 30 mg morphine equivalence widely accepted through 2017. Compare with the previous week of 2.00 mg total daily buprenorphine which is equal to 60 mg morphine. This is a drop in a week of 0.02 mg buprenorphine which is equal to 0.6 mg morphine decrease. This small reduction attends to the reality of sensitivity to opioid dose-reduction at low doses.

99 (ninety-nine) additional actions: Continue with the portion-removal/reconstitution method, at each step removing 1 (one) kg of mixture of active/inactive mixture and reconstituting batch to 100 kg. This protocol produces successive batches of material in which 100 mg contains successive less amounts of buprenorphine in the amount of 0.0050 mg. At each step, process the removed 1 kg into 10,000 doses, expecting minor loss after processing the removed one kg due to residue in manufacturing equipment. The gross weight of every dose is 100 mg. As noted, the regimen requires 28 identical doses per week. 10,000 doses will therefore provide for treatment of 357 individuals for one week (10,000 doses/28 doses/week). A starting batch of 103 kg, through all one hundred dilutions/reconstitutions will likewise provide for about 357 individuals per 0.515 (zero point five one five) kg buprenorphine. Larger batches may yield labor savings on portion-removals/reconstitutions, offset by equipment costs. To provide medication for 357,000 (three hundred and fifty-seven thousand) individuals would require 515 (five hundred and fifteen) kg of buprenorphine and the capacity to process 103,000 (one hundred and three thousand) kg, or 51.5 (fifty-one and one-half) short tons, of mixture over time.

Continuing the portion-removal/reconstitutions, after the $100^{th}$ portion-removal/reconstitution, the dose that will be produced will contain 0.005 mg per 100 mg dose. At q.i.d., this equals a daily total of 0.02 (two one-hundredths) mg buprenorphine (MME 0.6 (six-tenths) mg morphine).

Action: After the $100^{th}$ reconstitution, that is, after adding 1 (one) kg of inactive ingredient 100 times and then removing 1 kg 100 times, from which is made 10,000 doses, then add 101 (one hundred and one) kg of inert mixture and mix this resultant 200 kg mass to homogeneity. This batch will yield doses of 100 mg each that each contain 0.0025 mg of buprenorphine per 100 mg dose. Remove 10 (ten) kg of this 200 kg of mixture. This is made into 10 times the doses of each previous week (with the exception of the first 4 kg removed which provided four weeks, i.e., 40,000 doses) and thereby provides ten weeks of 0.0025 mg/100 mg dose. With q.i.d. administration, 0.0025 mg times 4 equals 0.01 (one one-hundredth) mg total buprenorphine per day.

The remaining 190 kg of mixture is used to make 0.01 mg doses for other regimens that have a protocol in which 0.0025 mg/100 mg doses are more complex to manufacture, or used for some as yet undetermined market or use, perhaps as doses for maintaining what may likely be in large part a psychological effect with a small but real residue of physiological dependence. This completes manufacture using the described dilutions of 114 weeks of doses containing active ingredient. There follows production of doses for four weeks containing no active ingredient.

Weeks 105 through 114 represent a subsequent continuation of the dosing of week 104 with week 105 being the first time in 100 weeks there is no dose reduction at the end of each seven days, as are weeks 106 through 114.

The last four weeks of the 118-week regimen, Weeks 115 through 118, prescribed treatment with no active ingredient, are the same as the last four weeks of the 218-week regimen, described below, following description of weeks of 215-218.

Manufacture of the 218-Week Regimen:

The portion-removal/reconstitution approach to manufacture of the 218-week regimen uses the same principles as the 118-week manufacture protocol and can also be adapted to a range of dose reductions, varying only the ratio of active ingredient to inactive ingredients, in this case the proportion of buprenorphine to pharmacologically inert filler(s)/binder(s)/diluent(s). The portion-removal/reconstitution steps are quantitatively different for the 218-week embodiment compared with the 118-week embodiment.

Manufacture protocol for the 218-week protocol: The following procedure will produce a two-hundred week series (within the 218-week protocol) in which each week the daily total dose is reduced by 0.01 mg. Also produced are the four weeks of equal doses for 2 mg/day stabilization. In the 218-week regimen, 10 weeks of 0.0025 mg q.i.d. are manufactured as described above during the production of the 118-week regimen.

As with the 118-week regimen, the 218-week total daily dose is reduced once every week (7 days). In the 218-week regimen, the amount of weekly reduction is 0.01 mg buprenorphine, as opposed to 0.02 mg/week reduction in the 118-week regimen. The total daily dose in the 218-week regimen is comprised of four, every 6-hour, doses. The rate of reduction is 0.0025 mg per week of each q.i.d. dose. This is equivalent to 0.01 mg reduction of buprenorphine per week, i.e. 4×0.0025 mg=0.01 mg. For example, an individual at a dosage level of 1.000 mg total a day, that is, each q.i.d dose is 0.2500 mg, during week X, will, in week X+1, have a daily total dose of 0.9900 mg and each q.i.d. dose will be 0.2475. This is a reduction of 0.0025 per dose per week which is equal to 0.01 mg buprenorphine reduction per day, each week. A dose reduction in excess of 0.01 mg/week is herein accepted as capable of producing, or contributing to, withdrawal sensations in a finite percentage of the addicted population. This amount of reduction may be considered an inconsequential change by some clinicians. The above notwithstanding, the structure of this invention accepts the promulgated view that a person who has taken opioids for many years may relatively often require a period of time equal to two or four years, or more, to reduce to abstinence from a low level of opioid, such as 2.0 mg of buprenorphine. Once this is accepted, arithmetic dictates the regimen. Reducing from 2 (two) mg/day of buprenorphine in approximately four years, or 218 weeks, is described herein from a the perspective of dose reduction, dose manufacture, packaging, pharmacology and other parameters of this invention.

The following protocol results in a series of doses that reduce weekly by 0.0025 mg per 100 mg tablet. Sub-lingual lozenges, liquids, gels, films or other delivery materials are considered as equivalent when this interval of dosage reduction is employed. All standard manufacturing protocols necessary to ensure that the mixtures are totally homogeneous throughout are employed. As above, moisture content must be maintained within the tolerances required to avoid significant dosage variations, since production using this method may stretch out over a period of time.

The degree of precision that can be achieved during this manufacture protocol may vary depending upon the equipment, instrumentation and skill levels of various manufacturers and relies upon accurate and consistent analytic balances, precision mixing and unit manufacture, experience levels, assaying and moisture control. As detailed, relative consistency of dose reduction can be achieved so long as precision can be maintained and has the advantage that manufacture thereby avoids milligram measurements to unrealistic tolerances.

Action: To manufacture the series of doses for the 218-week regimen, take 1.015 kg (one point zero one five kilograms) of buprenorphine and 201.985) two hundred and one point nine eight five) kg of filler/binder/diluent pharmacologically inert ingredients normally used to make tablets containing the active ingredient of buprenorphine. The total mass is 203.000 (two hundred and three) kg, mixed to create a totally homogenous compound mixture.

Action: Remove 4 (four) kg of said 203 kg mixture. Each of these 4 kg contains 0.005 kg of buprenorphine per kg of mixture. With 0.005 (kilogram) kg buprenorphine/kilogram of compound equating to 0.005 (milligram) mg/milligram of compound. This results in 0.5 (milligram) mg buprenorphine/100 (milligram) mg tablet. Consumption of four doses per day of 0.5 mg buprenorphine, results in a daily total of 2.00 mg buprenorphine. This is same start point as 118-week regimen described above.

Action: The said removed 4 (four) kg are then processed using established methods for making doses from a compounded mixture of active/inert ingredients, as are the amounts subsequently removed, one kg per step, as described here. To vary output quantities, the amounts (quantities) described here may be multiplied or divided by any practical production number, provided all amounts are multiplied by same factor and provided the equipment and processing do not distort or negatively impact the product composition based on lot size being processed or attempts at unrealistic masses of product.

The novel aspect here is, as with the shorter regimen of 118 weeks, in the formula for making the successive dilutions such that micro-differences, i.e., in an approximate range of 0.0015 mg to 0.0075 mg between successive weekly doses, not previously practical to produce, may be mass-produced to yield a tapered opioid regimen. The doses for the first four weeks of necessary stabilization are each 0.5 mg, q.i.d, for 2.0 mg/day total, although production may be modified to any starting dose, while maintains the dosage increments described herein. For Week #5, which is the first weekly step down, the total daily dose is 1.99 mg. This means each q.i.d dose is 0.4975 mg (4×0.4975 mg=1.99 mg). After the 4 (four) kg are removed from the 203 kg of compound, there remains 199 kg of compound containing 0.995 kg of buprenorphine.

Action: To produce the q.i.d. dose of 0.4975 mg buprenorphine per 100 mg tablet, add 1 (one) kilogram of inert mixture to the 199 kilograms of compound mixture (active and inert ingredients) that remains after the first said 4 kg were removed from the 203 kg of active plus inert mixture. The 199 kg of compound mixture plus 1 kg of inert filler/binder/diluent yields a reconstituted mass of compound mixture of 200 kg that contains 0.995 kg buprenorphine. This produces a tablet with 0.4975 mg/100 mg.

The same general procedure, of removing one kilogram of compound and replacing this kg with 1 kg of inert filler/binder/diluent is then repeated to produce a 100 mg dose containing 0.4950 mg of buprenorphine which will commence at the start of the second week of reduced dosages, which is the beginning of the 6th week of the 218 week protocol. This reduction of 0.0025 mg, q.i.d, which is a 0.01 mg reduction of buprenorphine per week, is maintained for a period of 200 weeks and is a function of utilizing the production of this manufacturing protocol.

Action: To manufacture the 0.4950 mg doses, add 1 (one) kg of inert filler/binder to the 199 kg of compound remaining after the previous removal of one kg, which was utilized to produce the 0.4975 mg doses, producing 200 kg of compound.

Action: Repeat this process of removing one kg of the compound and replacing with one kg of inert ingredients a total of 200 times, including above two portion-removal/reconstitutions. With the ratios specified, one kg is processed into 10,000 doses per kg, minus minor amounts that will remain in equipment.

To produce this protocol, the amount of buprenorphine removed is continually calculated and the amount remaining in continually calculated, in the first three steps, producing 0.5000, 0.4975 and 0.4950 mg buprenorphine per 100 mg of compound tablet, here the following amounts of buprenorphine have been removed:
1) 0.02000 kg buprenorphine in 4 kg, producing 0.5000 mg/100 mg tablet.
2) 0.004975 kg buprenorphine in 1 kg, producing 0.4975 mg/100 mg tablet.
3) 0.004950 kg buprenorphine in 1 kg, producing 0.4950 mg/100 mg tablet.
This manufacturing process aligns with the parameters of the embodiment in which, each week, the dose is reduced by 0.0025 mg of buprenorphine per 100 mg dose. Following 200 repetitions of portion-removal/reconstitution, the final week contains 0.0025 mg buprenorphine/100 mg compound.

Weeks 205 through 214: The ten weeks at 0.01 mg buprenorphine total daily dose, i.e., 0.0025 mg q.i.d., are manufactured in excess when making the 118-week protocol for the dose of 0.01 that follows the $100^{th}$ week dose of 0.02 (two one-hundredths). See above. Using the protocol manufacturing for the 118-week protocol results in a large remainder of compound that is at the concentration to make 10 weeks at 0.0025 mg per q.i.d. dose, for total of 0.01 mg day total and this 0.0025 mg/100 mg dose is used here, followed by the placebo series described above as the final four weeks.

Terms: "Inert" ingredients throughout shall mean "binder/filler/diluent" as conventionally utilized in similar processes. "Add" or "adding" of inert ingredients shall mean "to add or adding in the conventional manner and proportions for the category of manufacture being performed."

Using the method of portion-removal/reconstitution it is possible for small deviations to enter into the process either mathematically (i.e., computationally) or mechanically, that are then carried from one step to the next. These deviations are not regarded as materially affecting the process and product, provided the relative ratio of the difference from week to week does not change, that is, relative reduction from week to week remains consistent, and provided the deviation is in the range of either $1/1000$ (one one-thousandth) of the intended dose or $1/10,000$ (one ten-thousandth) of a mg.

Alternative Manufacture Method to Portion-Removal/Reconstitution:

The alternative process to portion-removal/reconstitution is to utilize precise measurements to make 101 batches for the 118-week regimen and 200 batches for the 218-week regimen. The problem posed by not using the dilution process centers around the need to produce a series of steps in which the amount by which a dose is decreased is in the range of about 0.0010 to 0.0075 mg (milligrams) from one week to the next week. For example, if a patient's dose is 1.0000 mg per day and the patient is dosed q.i.d, then each dose that week is 0.2500 mg four times per day. In said 218-week regimen described herein, that means that with a reduction of 0.0025 mg per week, the q.i.d. dose the next period of seven days is 0.2475 mg, with daily dose being 0.9900 mg/day. In the said 118-week regimen described herein, where dose one week is 0.2500 mg four times per day, the q.i.d., dose the following seven days is 0.2450 mg, with daily total 0.9800 mg/day. These tolerances can be difficult to meet using a traditional approach that employs mixing a series of doses that require not just small tolerances to be met but that the starting ingredients must maintain a level of consistency that is not practical to maintain. Two examples of this traditional approach are provided. All doses are shown in Illustrations. To manufacture any other dose, follow principles of these two examples.

Action: To manufacture 10,000 doses of 0.2500 mg each: Mix 2.500 (two and one-half) kg (kilograms) of buprenorphine and 97.500 kg of inert filler/binder.

To manufacture 10,000 doses of 0.2475: Mix 2.475 kg of buprenorphine and 97.525 kg or inert filler/binder. Use conventional equipment and methods, mixing above two batches thoroughly to acceptable level of homogeneity and process into 100 mg tablets. Central requirements of this method are: 1) measuring kilogram masses within close to one milligram tolerance from batch to batch and 2) Consistent purity of buprenorphine utilized. If the purity of the buprenorphine differs significantly from batch to batch it creates significant issues using this method. When the difference is detected through assay, purity is corrected.

Using the above conventional approach, any dose of buprenorphine in the sequential regimen may be manufactured. For example, the last ten weeks of both the 118-week regimen and the 218-week regimen, require a q.i.d dose of 0.01 (one one-hundredth) mg. To manufacture 10,000 doses, take 0.01 (one-one-hundredth) kg (kilogram) of buprenorphine and 99.990 kg of inert filler/binder and process as above to mix and produce tablets of 100 mg each containing 0.01 mg buprenorphine.

The above proportions of buprenorphine may be employed using fillers/binders/diluents for film or liquid manufacture to make films for sub-lingual or buccal use. The above mass quantities may be multiplied to make larger or smaller batch quantities depending upon the capacity of available equipment. Throughout all processes herein described, moisture content is monitored and considered in any weight computation.

Manufacture Combining Units of Cut Film:

With a topically applied patch medication modality, or with a sublingual or buccal film, that is a uniform matrix of cuttable film, manufacture of said invention uses a fixed cut area of a sheet of medication of precisely known concentration of medication and combines as many pieces as needed to reach the dose. This is an alternative to mixing 101 or 200 different concentrations for film manufacture or having a sheet with one concentration and producing three or four doses, such as 8 mg, 4 mg and 2 mg or doses of 900, 750, 600 and so on down to 75 micrograms, in which the intervals between manufactured doses are orders of magnitude larger than present invention and admonitions are provided in the inserts not to divide the manufactured dose. The method for sheet division described herein is an alternative to providing sheets of different sizes, which has a built-in limitation as the dosage level becomes one-tenth or one-twentieth of the initial dose. The use of four different concentrations of the source sheet, however, when making a film or patch, allows size to be used to reduce dose, as described below.

Action: Utilize a sheet 10×10 centimeters (cm), or of any practical size, manufactured using established techniques for the manufacture of films that contain medication, to contain total of 1.0 mg of buprenorphine per 100 square centimeters. Cut 10 cm×10 cm of this film sheet into one hundred 1 cm squares or rectangles, with each square containing 0.01 mg of buprenorphine when the sheet is manufactured to be uniform throughout as regards concentration of medication. These squares/rectangles/pieces are combined to reach any desired dose up to 0.99 mg. This is applicable to sublingual/buccal formats. Films with lower doses will have smaller squares or will require fewer squares be combined. The principal is the same regardless of the shape of the piece of the larger film. The specifics of the exact dose reduction and timing of dosing using said embodiment is novel. This permits gradations of doses not otherwise economically achievable through proportional mixing of active/inactive ingredients. This section specifies the manner and process of making. March An alternative method to cutting and recombining is as follows: To manufacture buccal or sublingual films that will differ in dosage to the extent and with the precision of this invention, make sheets of film that contain different concentrations. Ten concentrations are made, such that a resultant cut film that is 1 cm×1 cm or 2 cm×2 cm will contain anywhere from 0.5000 to 0.0025 mg of buprenorphine, suitable for combining to make multiples of doses in the range of 0.5000 to 0.0025 mg of buprenorphine.

Ranges in a manufacture series are as follows; with it understood that 2 cm×2 cm is an example within a range that can be modified. Manufacture large sheets that contain, per 2×2 cm, the milligrams of buprenorphine, amounts in Column A, which can be used to make, through cutting and recombination, the range of doses in Column B:

| Column A<br>Amount<br>buprenorphine/film | Column B<br>Range of doses that can be<br>made from Column A film |
| --- | --- |
| 0.5000 | 0.4525-0.5000 |
| 0.4500` | 0.4025-0.4500 |
| 0.4000 | 0.3525-0.4000 |
| 0.3500 | 0.3025-0.3500 |
| 0.3000 | 0.2525-0.3000 |
| 0.2500 | 0.2025-0.2500 |
| 0.2000 | 0.1525-0.2000 |
| 0.1500 | 0.1025-0.1500 |
| 0.1000 | 0.0525-0.1000 |
| 0.0500 | 0.0025-0.0500 |

Column A shows the amount of buprenorphine in a specified area of the initial sheet of film. Column B shows the range of doses that can be made by precision cutting and combining of pieces. The process permits doses to differ by amounts as small, or smaller, than 0.0025 mg of buprenorphine so as to meet demands of small increments of reduction at low opioid doses if withdrawal symptoms are to be minimized or avoided.

These initial squares, rectangles, or shapes are cut so as to provide the appropriate dose. The calculation is done as follows: to produce a dose of 0.2050, take a film 9 cm$^2$ with a total amount of buprenorphine 0.2500 mg buprenorphine. The entire initial film contains 0.2500 mg buprenorphine in the 9 cm$^2$. This is 0.027778 mg of buprenorphine per cm$^2$. To obtain a dose of 0.2050, utilize 7.380 cm$^2$ of the 9 cm$^2$ film containing 0.2500 mg buprenorphine. This is a square that is 2.7166 cm on each side. Precision cutting is required. If required precision is not available, the ranges of column A are made smaller such that less precision is needed in make cuts. The ranges of Column A are suitable for manufacture of the 118- or 218-week regimens, during which dose reduction occurs for 100 and 200 weeks, respectively, as described herein. This is an advance. Films currently exist that are 75 micrograms (0.075 mg) apart in dosage level. The present invention permits production of doses that differ by 0.0025 mg which is a difference by a factor of 30 compared with current products. The small difference in dosages, at the 0.0025 mg level, permits a dosage regimen that aligns with the understanding of the emergence of withdrawal symptoms during dose reductions at very low doses.

Part of manufacture and distribution requires that a reserve of each week of a lot be retained to allow for replacement of lost or destroyed dispensed prescriptions. Due to the care with which most responsible patients conserve and store their opioid medication, this reserve will not need to be more than a few percent for lost or destroyed medication. The reserve is a finite amount that is not shipped or sold except as replacement. A finite amount is also reserved for patients who may be paused by their clinicians at a given dosage level. The invention is designed to avoid the need for pauses through use of adequately small dose reductions. Nevertheless, patients feeling that they are reducing too rapidly is a relatively common event and must be anticipated with any opioid taper product. Patients on protracted maintenance at the same level can feel the need to increase their dose. In terms of withdrawal, there are patients who are not candidates for any degree of dose reduction, regardless of how slow it may be, such as herein.

A central reason for all weeks and all replacements to come from the same manufacturing lot is that standard current manufacturing requirements that a product be within a certain percentage of other lots of the same medication may not be a demanding enough requirement to meet a 0.0025 or 0.0050 mg q.i.d. dose reduction per week.

What is claimed is:

1. A method of dividing and linearly tapering doses and administering opioids, comprising:
    providing patients with a medication with doses specifically intended, designed, and made to be consumed orally, a tablet or a film, for the purpose of treating individuals addicted to or dependent upon opioids, or diagnosed with opioid use disorder, for the purpose of reducing said individuals' opioid consumption to zero, between two and eight doses of buprenorphine opioid, at intervals of three to twenty-four hours, inclusive,
    administering said opioid, for an initial period of four or more weeks, a daily dose of between one and eight milligrams, at a constant dose;
    following said initial period with a second period of opioid administration with a duration of between 100 to 900 weeks, wherein a linear reduction once each week of the daily dose of said opioid in the range of a reduction from 0.002 to 0.030 milligrams per week, with administration continuing in divided doses between one time and eight times per day;
    following said second period of 100 to 900 weeks with a third time period having a duration of from five and 15 weeks, wherein a daily dosage of said opioid in the range of 0.0005 milligrams to 0.0200 milligrams per day, at the same dosage every day through entirety of period 3, is administered in divided doses from two to eight times per day;
    following said third period of five to 15 weeks with a fourth time period with a duration from four to eight weeks, wherein said daily dosage is a placebo containing zero milligrams of said opioid, administered four, three, two and one time(s) per day, each dose configuration of four, three, two or one time(s) per day to have a duration of at least one week.

2. A method of claim 1 of administering buprenorphine comprising: providing patients with a medication with doses specifically intended, designed, and made to be consumed orally, a tablet or a film, for the purpose of treating individuals addicted to or dependent upon opioids, or diagnosed with opioid use disorder, for the purpose of reducing said individuals' opioid consumption to zero, for an initial time period of four weeks, a daily dose of 2 mg/day total in four divided doses of 0.500 mg, four times per day, all daily total dosing being administered in four divided doses at six-hour intervals, throughout;
    administering, following said initial period with a second period, that being of 100 weeks duration, of buprenorphine wherein the linear reduction of buprenorphine is a 0.02 (two one-hundredths) milligrams reduction per week, of the daily dose;
    administering, following the said second period of 100 weeks, during a third time period having a duration of ten weeks, wherein a daily dosage of said opioid of 0.01 (one one-hundredth) mg/day in four divided doses per day of 0.0025 (twenty-five thousandths) milligrams;
    administering, following said third period with a fourth time period with a duration of four weeks, wherein said total daily dosage of opioid is zero mg and doses consist of doses identical in appearance, protocol and packaging to all previous active doses, with the exception that in the first of the final four weeks there are four inert doses per day, in the second of the four weeks there are three inert doses a day, in the third week being two inert doses a day, and in the final week of the taper regimen, there being one inert dose per day, doses during these four weeks being dispensed at six, eight, twelve and twenty-four hour intervals for the successive weeks respectively, with total administration being part of a taper regimen of 118 weeks.

3. A method of claim 1 of administering buprenorphine in a 218-week taper regimen, comprising:
    providing patients with a medication with doses specifically intended, designed, and made to be consumed orally, a tablet or a film, for the purpose of treating individuals addicted to or dependent upon opioids, or diagnosed with opioid use disorder, for the purpose of reducing said individuals' opioid consumption to zero, for an initial time period of four weeks, a daily dose of 2 mg/day total in four divided doses of 0.500 mg, four times per day, all daily total dosing being administered in four divided doses at six-hour intervals, throughout;
    administering, following said initial period with a second period, that being of 200 weeks duration, of buprenorphine, wherein the linear reduction of buprenorphine is a 0.01 (one one-hundredth) milligram reduction per week, of the daily dose, which is administered in four divided doses;
    administering, following the said second period of 200 weeks, during a third time period having a duration of ten weeks, wherein a daily dosage of said opioid of 0.01 (one one-hundredth) mg/day in four divided doses per day of 0.0025 (twenty-five thousandths) milligrams;
    administering, following said third period with a fourth time period with a duration of four weeks, wherein said total daily dosage of opioid is zero mg and doses consist of doses and dosing identical in appearance, protocol and packaging to all previous active doses, with the exception that in the first of the final four weeks there are four inert doses per day, in the second of the four weeks there are three inert doses a day, in the third week being two inert doses a day, and in the final week of the taper regimen, there being one inert dose per day, doses during these four weeks being dispensed at six, eight, twelve and twenty-four hour intervals for the successive weeks respectively, with total administration being part of a taper regimen of 218 weeks.

4. A method of manufacturing a taper regimen of opioid medication, said taper regimen comprising:
    starting with manufacture of a dose of medication in the range of one to eight milligrams (mg), intended for the initial period of four weeks or more, during which time this is the daily per day total, manufactured to be administered as four divided doses;
    manufacturing the medication for a range of 100 to 900 weeks, during said weeks the dose of opioid being reduced weekly in the range of 0.01 (one one-hundredth) to 0.03 (three one-hundredths) mg opioid;
    manufacturing medication for administration during the period following 100 to 900 weeks, of five to fifteen weeks duration, being a dose of 0.01 (one one-hundredth) mg opioid, manufactured as four divided doses of 0.0025 mg opioid, and;
    manufacturing medication to follow the five to fifteen weeks of 0.01 mg opioid total per day, by one to ten weeks of doubly unblinded inert doses, this final sequence completing any specific said taper regimen; wherein said manufacturing includes the steps of:

mixing to complete homogeneity 103 (one hundred and three) kilograms of a mixture consisting of 0.515 kilograms of buprenorphine, and 102.485 (one hundred and two point four eight five) kilograms, inert filler/binder/diluent;

removing 4.000 (four) kilograms of the 103 kg mixture (leaving 99 kg) with said 103 kg consisting of 0.5% active ingredient buprenorphine and 99.5% inactive mixture;

processing the 4.000 (four) kilograms that are removed, to manufacture 40,000 doses/tablets (minus normal manufacturing loss due to equipment adhesion or other cause) of 100 mg, each dose/tablet containing 0.500 mg of buprenorphine;

adding precisely one kilogram of the inert components: filler, binder, diluent to the above mass of 99 kilograms (kg) (the 103 kg mass above minus 4 kg removed) to reconstitute to 100 kg;

maintaining consistent moisture content through quantitative assay;

replicating the above protocol by performing 99 (ninety-nine) additional actions of continuing the portion-removal/reconstitution method, at each step removing 1 (one) kg of mixture of active/inactive mixture for processing into tablets/doses and then reconstituting the batch, with one kg of inert binder/filler/diluent, to 100 kg; processing at each step the removed one kg of compound into 10,000 doses, or multiples thereof;

continuing the portion-removal/reconstitutions, through the 100th portion-removal/reconstitution, with the dose being produced in the 100th step containing 0.005 (five one-thousandths) mg per 100 (hundred) mg tablet/dose;

adding 101 (one hundred and one) kg, immediately following the 100th portion-removal, of inert mixture;

mixing the resultant 200 (two hundred) kg mass to homogeneity, wherein said 200 kg batch is processed into doses of 100 mg that each contains 0.0025 (twenty-five ten-thousandths) mg of buprenorphine per 100 mg dose;

removing 10 (ten) kg of said 200 kg of mixture to produce a number of doses equal to ten times the number of each previous week thereby providing ten weeks of a 0.0025 mg/100 mg dose, and;

utilizing whatever portion of the remaining 190 kg of mixture is required for the final ten weeks of other regimens.

5. A method of manufacture of claim 4, of a taper regimen of doses of buprenorphine, with 98% of the reduction steps being in a linear fashion, with a duration of 118 weeks, wherein the manufactured product incorporates the following dosing requirements of starting at 0.5 (one-half) mg of buprenorphine, reducing manufactured doses in increments of 0.005 (five one-thousandths) mg of buprenorphine, and producing also doses of 0.0025 (twenty-five one-thousandths) mg of buprenorphine, comprising:

mixing to complete homogeneity 103 (one hundred and three) kilograms of a mixture consisting of 0.515 kilograms of buprenorphine, and 102.485 (one hundred and two point four eight five) kilograms of pharmacologically inert filler/binder/diluent;

removing 4.000 (four) kilograms of the 103 kg mixture (leaving 99 kg) with said 103 kg consisting of 0.5% active ingredient buprenorphine and 99.5% inactive mixture;

processing the 4.000 (four) kilograms that are removed, to manufacture 40,000 doses/tablets of 100 mg, each dose/tablet containing 0.500 mg of buprenorphine;

adding precisely one kilogram of the inert components: filler, binder, diluent to the above mass of 99 kilograms (kg) (the 103 kg mass above minus 4 kg removed) to reconstitute to 100 kg;

maintaining consistent moisture content through quantitative assay;

replicating the above protocol by performing 99 (ninety-nine) additional actions of continuing the portion-removal/reconstitution method, at each step removing 1 (one) kg of mixture of active/inactive mixture for processing into tablets/doses and then reconstituting the batch, with one kg of inert binder/filler/diluent, to 100 kg; processing at each step the removed one kg of compound into 10,000 doses, or multiples thereof;

continuing the portion-removal/reconstitutions, through the 100th portion-removal/reconstitution, with the dose being produced in the 100th step containing 0.005 (five one-thousandths) mg per 100 (hundred) mg tablet/dose;

adding 101 (one hundred and one) kg, immediately following the 100th portion-removal, of inert mixture;

mixing the resultant 200 (two hundred) kg mass to homogeneity, wherein said 200 kg batch is processed into doses of 100 mg that each contains 0.0025 (twenty-five ten-thousandths) mg of buprenorphine per 100 mg dose;

removing 10 (ten) kg of said 200 kg of mixture to produce a number of doses equal to ten times the number of each previous week thereby providing ten weeks of a 0.0025 mg/100 mg dose, and;

utilizing whatever portion of the remaining 190 kg of mixture is required for the final ten weeks of other regimens, this completing the manufacture of 114 weeks of doses containing active ingredient for a 118-week taper regimen.

6. A method of manufacture of claim 4 of medication for a taper regimen of doses of buprenorphine, with 99% of the reduction steps being in a linear fashion, with a duration of 218 weeks, wherein the manufactured product incorporates the following dosing requirements of starting at 0.5 (one-half) mg of buprenorphine, reducing manufactured doses in increments of 0.0025 (five one-thousandths) mg of buprenorphine, comprising:

combining, through thorough mixing, 1.015 (one and fifteen-thousandths) kilograms (kg) of buprenorphine and 201.985 (two hundred point nine eight five) kg of inert filler/binder/diluent, the total mass being 203.000 kg of totally homogenous compound mixture;

removing 4 (four) kg of this mixture, with each one kg of these removed 4 kg thereby containing 0.005 kg of buprenorphine per kg of mixture;

manufacturing from these removed 4 kg, 100 mg tablets, each containing 0.5 mg buprenorphine/100 (milligram) mg dose or tablet, suitable for the first four weeks of the 218 week regimen;

adding one kilogram of inert mixture to the 199 kg of compound mixture (said 199 kg consisting of active and inert ingredients as per immediately above) to make 200 kg of compound containing 0.995 (nine hundred and ninety-five thousandths) kg buprenorphine;

removing 1 kg from the 200 kg reconstituted mass and processing into 100 mg tablets each containing 0.4975 mg buprenorphine, suitable for week 5 of the 218-week regimen; repeating the same procedure and replacing the removed 1 (one) kg with 1 (one) kg of inert filler/binder/diluent to produce through manufacturing processes a 100 mg dose containing 0.4950 mg of buprenorphine, suitable for the start of the second week of reduced dosages, which is the beginning of the 6$^{th}$ week of the 218-week protocol;

repeating this protocol 197 additional times, of removing one kg of active/inert compound and replacing with one kg of inert ingredients, and making 100 mg tablets, with each step producing a tablet containing 0.0025 less of buprenorphine than the previous step, until;

producing in the final portion-removal/reconstitution process, 0.0025 mg per 100 mg tablet, each being one-quarter of the four times per day 0.01 mg daily dose, thereby having completed manufacture of 200 successive doses, each reducing by the amount of 0.0025 mg of buprenorphine.

7. A method of manufacture of claim 4, of a taper regimen medication comprising the opioid buprenorphine in a uniformly saturated matrix of precisely cuttable film, suitable for sublingual or buccal use, of precisely known concentration; taking said film and cutting into smaller pieces, each now containing a precisely known amount of buprenorphine, including taking a sheet 10 cm×10 cm, containing 1.0 mg of buprenorphine total, or a sheet of film of any size with a known concentration of buprenorphine; cutting, the 10 cm×10 cm sheet into one hundred pieces of each 1 cm$^2$, each square containing 0.01 mg of buprenorphine; combining these cut pieces so as to obtain any desired dose that is a multiple of 0.01 mg; initial sheets of different concentrations containing 0.5000, 0.4500, 0.4000, 0.3500, 0.3000, 0.2500, 0.2000, 0.1500, 0.1000, 0.0500 mg of buprenorphine are cut for dose ranges respectively of 0.4525-0.5000, 0.4025-0.4500, 0.3525-0.4000, 0.3025-0.3500, 0.2525-0.3000, 0.2025-0.2500, 0.1525-0.2000, 0.1025-0.1500, 0.0525-0.1000, 0.0025-0.0500 mg buprenorphine and combining said cut pieces for buccal or sublingual administration to produce any desired dose that is a multiple of 0.01 mg buprenorphine.

* * * * *